US009138374B2

(12) United States Patent
Tapadiya

(10) Patent No.: US 9,138,374 B2
(45) Date of Patent: *Sep. 22, 2015

(54) IRRIGATION FLUID COLLECTION BASINS THAT RECEIVE PORTIONS OF THE HUMAN ANATOMY

(71) Applicant: Dilip Tapadiya, Newport Beach, CA (US)

(72) Inventor: Dilip Tapadiya, Newport Beach, CA (US)

(73) Assignee: Dilip Tapadiya, M.D., Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/268,448

(22) Filed: May 2, 2014

(65) Prior Publication Data

US 2014/0237716 A1 Aug. 28, 2014

Related U.S. Application Data

(63) Continuation of application No. 10/776,309, filed on Feb. 11, 2004, now Pat. No. 8,968,262.

(60) Provisional application No. 60/498,926, filed on Aug. 29, 2003, provisional application No. 60/446,649, filed on Feb. 11, 2003.

(51) Int. Cl.
*A61M 1/00* (2006.01)
*A61H 35/00* (2006.01)
(Continued)

(52) U.S. Cl.
CPC .............. *A61H 35/00* (2013.01); *A61M 3/0279* (2013.01); *A61M 3/0287* (2013.01); *A61B 19/42* (2013.01); *A61M 2210/083* (2013.01); *A61M 2210/086* (2013.01)

(58) Field of Classification Search
USPC ......... 604/317–329, 332, 335, 346–347, 349, 604/355–356
See application file for complete search history.

(56) References Cited

U.S. PATENT DOCUMENTS 44,448 A 9/1864 Olmsted
2,709,435 A 5/1955 Kress
(Continued)

FOREIGN PATENT DOCUMENTS

FR 2643875 9/1990
WO WO 2004/071554 8/2004

OTHER PUBLICATIONS

International Search Report dated Apr. 26, 2006 for PCT Application No. PCT/US04/03795.
(Continued)

*Primary Examiner* — Michele M Kidwell
(74) *Attorney, Agent, or Firm* — Knobbe, Martens, Olson & Bear, LLP

(57) ABSTRACT

Various embodiments of irrigation fluid collection basins are disclosed. The basin is configured for irrigation of a wound or fracture generally located on a portion of the human anatomy, such as a knee, shin, calf, elbow, or otherwise. The basin can include two recesses located on opposite sides of the basin along an upper periphery of the basin. The recesses are configured to receive the portion of the human anatomy (e.g., a leg) at two regions proximal to the location of the wound or fracture, so that the wound or fracture is located over the cavity of the basin. The recesses can be sized so that one is broader than the other, the broader recess configured to comfortably accommodate a larger region of the leg and the other recess configured to comfortably accommodate a smaller region of the leg.

5 Claims, 22 Drawing Sheets

(51) Int. Cl.
*A61M 3/02* (2006.01)
*A61B 19/00* (2006.01)

(56) References Cited

U.S. PATENT DOCUMENTS

| | | |
|---|---|---|
| D174,990 S | 6/1955 | Horn, Jr. |
| 3,015,110 A | 1/1962 | Treand |
| 3,083,376 A | 4/1963 | Johns |
| D197,106 S | 12/1963 | Laubsch |
| 3,288,140 A | 11/1966 | McCarthy |
| 3,407,957 A | 10/1968 | Robinson |
| 3,460,164 A | 8/1969 | Patton |
| D220,928 S | 6/1971 | Bost |
| D240,767 S | 7/1976 | Lemelson |
| 4,024,590 A | 5/1977 | Wendt |
| D251,202 S | 2/1979 | Charewicz |
| 4,368,548 A | 1/1983 | Glass |
| 4,692,140 A | 9/1987 | Olson |
| 4,769,003 A | 9/1988 | Stamler |
| 4,834,068 A | 5/1989 | Gottesman |
| 4,925,047 A | 5/1990 | Valentine et al. |
| 5,224,940 A | 7/1993 | Dann et al. |
| 5,245,713 A | 9/1993 | Tickle |
| D347,058 S | 5/1994 | Valentine |
| 5,312,385 A | 5/1994 | Greco |
| 5,316,541 A | 5/1994 | Fischer |
| 5,381,562 A | 1/1995 | Holloway et al. |
| 5,393,299 A | 2/1995 | Brettin |
| 5,477,866 A | 12/1995 | Davenport |
| 5,496,290 A | 3/1996 | Ackerman |
| 5,579,543 A | 12/1996 | Crawford et al. |
| 5,582,165 A | 12/1996 | Bryan et al. |
| 5,609,163 A | 3/1997 | Beard |
| D386,684 S | 11/1997 | Marogil |
| 5,697,921 A | 12/1997 | Blair |
| 5,735,833 A | 4/1998 | Olson |
| 5,792,125 A | 8/1998 | Webb |
| D398,075 S | 9/1998 | Book et al. |
| 5,848,998 A | 12/1998 | Marasco, Jr. |
| 5,941,859 A | 8/1999 | Lerman |
| 5,946,745 A | 9/1999 | Magee |
| 5,947,894 A | 9/1999 | Chapman et al. |
| 5,989,281 A | 11/1999 | Barbut et al. |
| 6,050,981 A | 4/2000 | Lampropoulos et al. |
| 6,083,209 A | 7/2000 | Marasco, Jr. |
| 6,085,769 A | 7/2000 | Poyner et al. |
| 6,093,182 A | 7/2000 | Lampropoulos et al. |
| 6,156,004 A | 12/2000 | Tremaine et al. |
| 6,189,162 B1 | 2/2001 | Tanner |
| 6,210,382 B1 | 4/2001 | Hogg |
| 6,287,289 B1 | 9/2001 | Niedospial, Jr. |
| 6,293,929 B1 | 9/2001 | Smith et al. |
| 6,311,838 B1 | 11/2001 | Johnson et al. |
| 6,398,062 B1 | 6/2002 | Jones |
| 6,402,724 B1 | 6/2002 | Smith et al. |
| 6,405,389 B1 | 6/2002 | Harty |
| 6,406,447 B1 | 6/2002 | Thrash et al. |
| 6,458,109 B1 | 10/2002 | Henley et al. |
| 6,558,344 B2 | 5/2003 | McKinnon et al. |
| 6,609,257 B1 | 8/2003 | O'Geary |
| 6,755,196 B2 | 6/2004 | Musso et al. |
| 6,935,341 B2 | 8/2005 | Musso et al. |
| 7,785,303 B2 | 8/2010 | Tapadiya |
| 994,884 A1 | 6/2011 | Stewart |
| 1,061,769 A1 | 5/2013 | Meinecke |
| 2002/0083516 A1 | 7/2002 | Wing et al. |
| 2003/0062281 A1 | 4/2003 | Giard, Jr. et al. |
| 2004/0055919 A1 | 3/2004 | Rowe et al. |
| 2004/0060566 A1 | 4/2004 | Musso et al. |
| 2004/0225266 A1 | 11/2004 | Tapadiya |
| 2004/0225267 A1 | 11/2004 | Tapadiya |
| 2006/0011506 A1 | 1/2006 | Riley |

OTHER PUBLICATIONS

Written Opinion of the International Search Authority in related International Patent Application No. PCT/US04/03795, dated Apr. 26, 2006.
International Preliminary Report on Patentability in related International Patent Application No. PCT/US04/03795, dated May 22, 2006.
Office Action in related Canadian Patent Application No. 2515657, dated Sep. 6, 2011, in 3 pages.
Examination Report in related European Patent Application No. 04709839.7, dated Jan. 14, 2011.
Examination Report in related European Patent Application No. 04709839.7, dated Dec. 20, 2011.
Examination Report in related European Patent Application No. 04709839.7, dated Apr. 30, 2013, in 4 pages.
Office Action in related Canadian Patent Application No. 2515657, dated Jun. 19, 2012, in 3 pages.
Office Action in related Canadian Patent Application No. 2515657, dated Apr. 25, 2013, in 2 pages.
Office Action in related Canadian Patent Application No. 2515657, dated Jan. 2, 2014, in 3 pages.

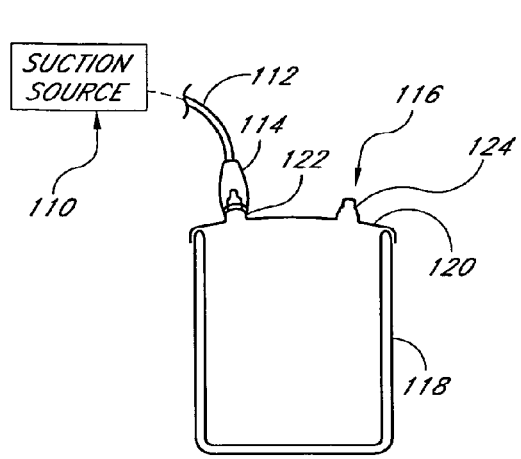
FIG. 14
(PRIOR ART)
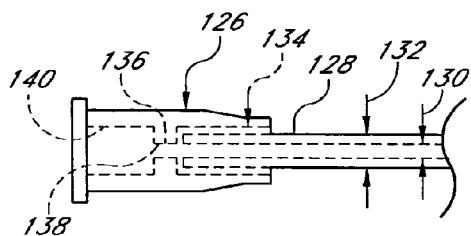
FIG. 15
(PRIOR ART)
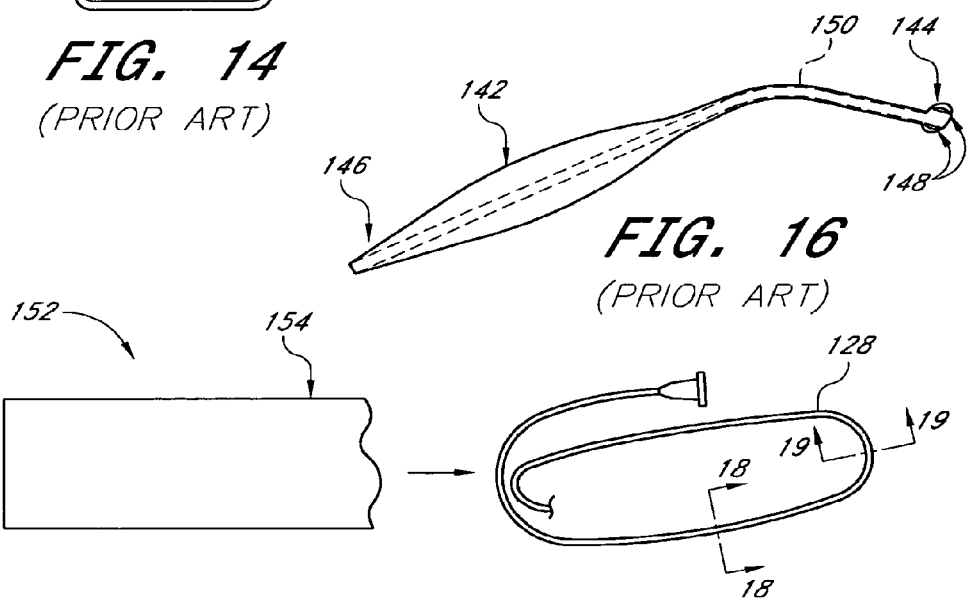
FIG. 16
(PRIOR ART)
FIG. 17
(PRIOR ART)
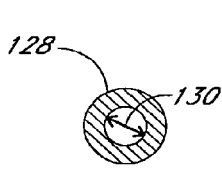
FIG. 18
(PRIOR ART)
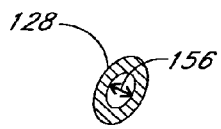
FIG. 19
(PRIOR ART)
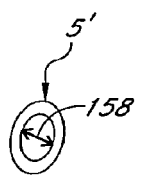
FIG. 20

IRRIGATION FLUID COLLECTION BASINS THAT RECEIVE PORTIONS OF THE HUMAN ANATOMY

CROSS REFERENCE TO RELATED APPLICATIONS

This application is a continuation of U.S. application Ser. No. 10/776,309, filed Feb. 11, 2004, which claims the benefit of U.S. Provisional Application No. 60/498,926, filed Aug. 29, 2003 and of U.S. Provisional Application No. 60/446,649, filed Feb. 11, 2003, the entireties of which are incorporated herein by reference.

BACKGROUND OF THE INVENTION

1. Field of the Invention

The present inventions are directed to surgical equipment, and in particular, equipment used for irrigating wounds on the human body.

2. Description of the Related Art

Basins are widely used in the medical field to collect irrigation fluid during an irrigation procedure of a wound on a patient. The wound may consist of a laceration or a cut that breaks a skin surface. Fractures may also require irrigation procedures. Medical personnel irrigate such wounds to flush out any contaminants from the wound prior and/or subsequent to conducting a medical procedure on the wound area.

Irrigation procedures are common in the medical field, particularly in the field of orthopedic surgery, due to the fact that wounds are fairly common injuries, many of them requiring treatment at a medical facility, particularly deep cuts. Therefore, medical facilities tend to maintain a significant number irrigation kits ready for use during surgical procedures. This is also true for emergency room facilities, where patients with wounds requiring immediate treatment generally arrive, and where the number of patients that will arrive throughout a day is impossible to predict. However, the use of irrigation kits is not limited to emergency room procedures and includes other medical procedures as well.

Existing irrigation kits typically include at least one basin to collect the irrigation fluid wrapped in plastic or other material preventing dirt or other contamination from coming in contact with the basin. Wrapping the kit in plastic also allows the kits to be kept separate from each other, even if the kits are stacked one on top of another. Moreover, each kit generally includes various components necessary for an irrigation procedure so that medical personnel usually need not open more than one irrigation kit to perform an irrigation procedure. The components, such as the basins, are usually sterilized.

When a wound requires irrigation, medical personnel open an irrigation kit to take the basin out of the kit, and place the basin in an area below the region of the patient's body where the wound is located. Then, with an irrigation device, the medical personnel directs an irrigation fluid, such as, but without limitation, water, saline, or a solution including antibacterials and/or antibiotics at the wound area to remove contaminants, tissue and/or bone fragments from the wound.

The irrigation device preferably delivers irrigation fluid at a pressure and flow rate sufficient to effectively clean the wound area. The irrigation device may have a shield connected to the device to reduce the amount of irrigation fluid that splashes off the wound field and/or in the direction of the treating medical personnel or on the floor. The shield can further be used to focus the direction of the irrigation fluid on the wound when the device is placed close to the wound area.

Throughout the irrigation procedure, medical personnel adjust the location of the basin to collect the irrigation fluid after it strikes the wound area. For example, one may place the basin just below the body part where the wound is located. Alternatively, one may place the basin in a location to which the irrigation fluid flows after striking the wound area.

SUMMARY OF THE INVENTION

One aspect of at least one invention disclosed herein includes the realization that a significant amount of labor is unnecessarily wasted during medical irrigation procedures. For example, in a typical irrigation procedure, an open wound or fracture is irrigated with an irrigation device that discharges a stream of irrigation fluid. Typically, a doctor or surgeon manually aims the stream of irrigation fluid into the wound in order to dislodge and flush out contaminants, tissue and/or bone fragments. Occasionally, irrigation fluid will splash out of the wound when the stream of irrigation fluid strikes tissue or bone.

The amount of irrigation fluid used for such procedures varies. For example, more irrigation fluid is used for irrigating larger wounds than that used for irrigating smaller wounds. However, the amount of irrigation fluid used may also vary depending on the depth of the wound, e.g., more irrigation fluid being used for deeper wounds. Additionally, the amount of irrigation fluid used may also vary depending on the type and risk of potential contamination. For example, where a wound was partially created during an accident such as impalement, more irrigation fluid may be used compared to that used to irrigate a wound created by a surgeon during a planned procedure or other surgical procedures. Finally, a surgeon may decide to irrigate one wound more than another for various other reasons, such as, but without limitation, the amount of time the wound was open. Thus, it can be difficult to predict the amount of irrigation fluid that will be used to irrigate a wound.

During irrigation procedures performed for orthopedic surgery or other major medical procedures, a large amount of irrigation fluid is often used, e.g. one to ten liters. Thus, the basin used for collecting the irrigation fluid must be emptied repeatedly, requiring the irrigation procedure to stop, unless additional personnel and/or basins are used. As a full basin is removed, and an empty basin is re-positioned, some irrigation fluid inevitably is spilled on the floor, thus requiring additional towels and cleaning equipment to be used to keep the floor clean. If the towels or equipment is to be re-used, they must be sterilized.

An additional consideration with conventional basins is the potential for contamination of medical personnel with the bodily fluids of the patient that are collected in the basin during an irrigation procedure. If the irrigation fluid in the basin is spilled, the irrigation fluid, soft tissue, bone, and other debris contained therein may come in contact with medical personnel, exposing the personnel to contaminated and potentially infectious matter. Such an exposure can result in the transmission of diseases.

Thus, one aspect of at least one of the inventions disclosed herein includes the realization that a basin that can be used alone or quickly modified to be actively drained can decrease the risk of transmission of disease and save a significant amount of labor normally associated with surgical irrigation procedures. Such a basin can reduce the number of medical personnel needed for an irrigation procedure and the total man-hours required for the procedure.

Thus, in accordance with one embodiment of at least one invention disclosed herein, a basin comprises a sidewall portion and a bottom portion, at least one of the sidewall and bottom portions including at least one convertible portion configured to provide a substantially leak-proof barrier in a first state and to form a drain in a second state through which the basin can be drained, such as, for example, but without limitation, a suction hose commonly used in operating rooms.

By including at least one convertible portion in the basin, the basin achieves the dual goals of providing a conventional multi-purpose basin, and providing a basin that can be modified for use during a large volume irrigation procedure. For example, the basin can have any conventional shape, including for example, but without limitation, round, square, rectangular, oval, C-shaped, L-shaped, and kidney. Thus, the basin can be used for irrigation procedures just as any conventional basin is used, as well as non-irrigation related uses such as the temporary placement of instruments or devices. Additionally, the convertible portion can be modified to drain the basin. As such, the basin provides a more convenient device for collecting and discarding irrigation fluid used during an irrigation procedure.

For example, in one embodiment the convertible portion includes a frangible portion, which can be broken to form an aperture. A suction hose commonly used in an operating room can be connected to the aperture formed by the broken frangible portion. Thus, personnel handling the basin will not have to stop the irrigation procedure to empty the basin, and are less likely to spill any irrigation fluid, either on the floor or on themselves, during the procedure.

In accordance with another embodiment of at least one of the inventions disclosed herein, a wound irrigation kit comprises a grommet that can be readily fitted onto a basin in the kit to allow for draining of the basin during the irrigation procedure. Accordingly, the kit is advantageously versatile, allowing the basin to be used without the grommet for a shortened irrigation procedure, as well as allowing the basin to be readily modified to incorporate the draining attachment for a prolonged irrigation procedure. The grommet is defined by an axis and comprises a fitting part, a sealing part and a channel disposed in the center of the fitting and the sealing part along the axis. The fitting part is configured to be inserted through the convertible portion of the basin so that the sealing part of the grommet forms a substantially watertight seal with the wall of the basin facing the cavity of the basin. The fitting part protrudes out of the body of the basin in a direction away from the basin body. The fitting part also comprises an outer surface configured to securely receive a draining hose for active draining of the basin.

In accordance with another embodiment of at least one of the inventions disclosed herein, a wound irrigation kit comprises a cannula optionally having an adhesive surface. The cannula can optionally be made of flexible rubber. In another option, the cannula can be made of a hard plastic. Additionally, the cannula can optionally be configured to have a specific shape, such as, but without limitation, a C-shape, a Z-shape and an L-shape. The adhesive surface can optionally comprise flange integrally formed with the cannula. In another option, the adhesive surface can comprise the outer surface of the cannula itself.

In another embodiment of at least one of the inventions disclosed herein, a basin is configured for irrigation of a wound generally located on a knee area of a human leg. For example, the wound may be located on the leg over a kneecap. Additionally, the wound may be located on an upper shin or a lower quadriceps region of the leg, proximally located to the knee area. Use of the basin is not limited to wounds located on a front side of the leg, where the front side is defined as the side on which the knee-cap is located. The basin can also be used in irrigation procedures on a side of the knee or a region behind the knee. Additionally, the basin can be used in irrigation procedures on a wound on an upper calf or a lower hamstring region of the leg, proximally located to the knee area of the leg. Further, the basin can also be used for irrigation procedures on open fractures of other lower extremities.

The basin advantageously includes two recesses located on opposite sides of the basin along an upper periphery of the basin. The recesses are configured to receive the leg at two regions proximal to the location of the wound or fracture, so that the wound or fracture is located over the cavity of the basin. Specifically, the recesses are sized so that one is broader than the other, the broader recess configured to comfortably accommodate a larger region of the leg and the other recess configured to comfortably accommodate a smaller region of the leg.

For example, the recesses are configured to receive a shin and a thigh portion of the leg. If the wound is located on the kneecap, the recesses disposed on the upper periphery of the basin are capable of receiving the lower quadriceps region and the upper calf region of the leg. Moreover, one of the recesses is sized broader than the other recess, wherein the broader recess is sized to receive the thigh portion and the other recess is sized to receive the shin portion of the leg. Further, the recesses are preferably contoured in shape to comfortably receive the shin and thigh portions. The recesses advantageously allow the basin to more effectively collect the irrigation fluid used to irrigate a wound on the knee region during an irrigation procedure.

In still another embodiment of at least one of the inventions disclosed herein, a basin is configured for irrigation of a wound generally located on a human elbow region. For example, the wound may be located on either side of the elbow. Additionally, the wound may be located on a biceps region, a triceps region or a forearm region proximal to the elbow.

The basin for use in irrigation of a wound on the elbow region also has two recesses on the upper periphery for receiving two regions of the arm. The recesses are further configured to more effectively collect the irrigation fluid used to irrigate a wound on the elbow region during an irrigation procedure.

In another embodiment of at least one of the inventions disclosed herein, a basin is configured for irrigation of a wound generally located on a human ankle region. For example, the wound may be located on either side of the ankle. Additionally, the wound may be located on a lower shin or a lower calf region of the leg proximal to the ankle.

The basin for use in irrigation of a wound on the ankle region (i.e., ankle-basin) is configured similarly to the basin used to irrigate a wound on the elbow region (i.e., elbow-basin). The ankle-basin preferably has a taller sidewall and differently sized recesses than the elbow-basin. Specifically, the ankle-basin has two recesses on the upper periphery for receiving two regions of the leg proximal to the ankle. The recesses are configured to more effectively collect the irrigation fluid used to irrigate a wound on the ankle region.

In another embodiment of at least one of the inventions discloses herein, a basin comprises three recesses on the upper periphery. The first and third recesses are optionally sized to receive a human leg, while the second recess is sized to receive a human upper arm. Therefore, according to this embodiment, the basin can be used to irrigate wounds on the knee and elbow regions. Similarly, the second recess can optionally be sized to receive a human foot. Therefore, according to this embodiment, the basin can be used to irrigate wounds on the knee and ankle regions.

In still another embodiment of at least one of the inventions disclosed herein, a basin can have four recesses. The recesses can optionally have the same dimensions. In another option, only three of the four recesses can have the same dimensions. In still another option, only two of the recesses can have the same dimensions. In yet another option, the recesses can each have different dimensions. Accordingly, the basin can be configured to receive various parts of human extremities.

In another embodiment of at least one of the inventions disclosed herein, a basin comprises one recess on the upper periphery of the basin. The recess is preferably configured to receive a human extremity. For example, the recess can be configured to receive a human forearm to irrigate wounds located below the elbow. In another example, the recess can be configured to receive a human thigh region to irrigate wounds located below the knee. The height of the basin sidewalls is greater if the basin is used to irrigate leg wounds than if it is used to irrigate arm wounds.

In another embodiment of at least one of the inventions disclosed herein, a basin is configured for irrigation of a wound on a human shoulder. The wound can be located on an upper arm region near the juncture of the arm with the shoulder. The wound can also be located on a shoulder blade region or a pectoral region near the juncture with the arm.

The basin is preferably generally C-shaped, which advantageously allows the basin to be fitted around the upper arm region proximal to the wound. However, the basin can optionally have other shapes, such as, but without limitation, oval, round, square, kidney and horseshoe. The basin is further configured to have a contact region on an outer surface of the basin, wherein the contact region is advantageously configured to fit against a portion of a circumference of the upper arm. Accordingly, the basin is configured to more effectively collect the irrigation fluid used to irrigate a wound on the shoulder region during an irrigation procedure.

In yet another embodiment of at least one of the inventions disclosed herein, a basin is configured for irrigation of a wound on a human hip. The wound may be located on a buttock region or a lower hip region near the juncture with the buttock.

The basin advantageously has a contact region formed on the upper periphery of the basin. Moreover, the contact region advantageously makes substantial contact with the human anatomy from just above a hip to just below a buttock. Further, the contact region is advantageously recessed downward relative to the upper periphery of the basin, allowing the upper periphery to operate as a splash shield during the irrigation procedure.

Another embodiment of at least one of the inventions disclosed herein includes providing a flexible irrigation shield that can be attached to an irrigation device, such as the irrigation device shown in U.S. Pat. No. 6,156,004. The shield can also be readily modified to vary its length. Such a shield advantageously allows medical personnel to vary the splash-prevention area as needed for a specific irrigation procedure. The irrigation shield can have a variety of shapes. For example, the shield can be in the shape of a circle or a square. The shield can also be made of a variety of materials. For example, the shield can be made of a clear plastic.

Still another embodiment of at least one invention disclosed herein is directed to an irrigation kit that provides a plurality of the components useful for an irrigation procedure. The kit includes a plurality of basins, each basin configured to receive a body part that is to be irrigated to more effectively collect an irrigation fluid in the basin. Each basin comprises a body with a base and at least one wall defining a cavity configured to collect irrigation fluid. Additionally, each basin is advantageously configured to be readily modified for active draining of the basin. Each basin optionally has at least one convertible portion on the body, which may optionally be a frangible portion in the form of a circle. The convertible portion is preferably located near the bottom of the basin wall, wherein the convertible portion may be modified to form a drain. Further, the base of each basin is preferably slanted at an angle toward an end of the basin proximal to the convertible portion so that irrigation fluid collected in the basin advantageously rolls toward the drain formed on the basin body when the convertible portion is modified.

Another aspect of at least one of the inventions disclosed herein includes the realization that during certain types of surgery, such as for example, but without limitation, orthopedic surgery, the standard suction tubing commonly used suffers from a clogging problem that can be caused by constrictions that form in the tubing during packaging and storage. For example, typical operating rooms and other medical facilities use suction tubing having an inner diameter (I.D.) of about 5-6 mm in a relaxed state. Additionally, all of the components which are configured to be connectable with the 5-6 mm I.D. tubing, are sized and shaped so that they will only allow debris to pass into the suction tubing that is smaller than 5-6 mm.

During certain medical procedures, only liquids such as bodily fluids, humors, or irrigation fluid, is removed with a suction device. The typical 5-6 mm tubing does not suffer from a clogging problem when only liquids are being suctioned. However, during certain types of surgery, such as orthopedic surgery, for example, a significant amount of bodily tissues can be drawn into a suction device. It has been found that the conventional 5-6 mm I.D. tubing commonly used in operating rooms suffers from a bottle-necking problem, due in part to the packaging technique used in marketing the tubing. More specifically, the conventional 5-6 mm tubing commonly stocked for operating room use is folded into a sterilized package. The tubing is soft and flexible. Typically, the tubing is between 5 and 20 feet long. Thus, when the tubing is folded, the tubing collapses in the area of each fold. After the tubing has been stored for a significant amount of time, the collapsed portions of the tubing, usually in the area of the folds, remain in a partially collapsed state.

During an orthopedic operation, such as a joint replacement, many bone chips and clumps of tissue must be removed from the wound prior to closing. Thus, an orthopedic surgeon typically uses a small suction device having a suction tip with restricted openings, to suck out irrigation fluid, clumps of tissue, and bone chips. The restricted openings are sized so as to prevent large clumps of tissue and bone fragments from entering the suction hose. However, despite the size of the restricted opening, tissue clumps and bone fragments pass through the restricted opening which are large enough to form clogs at bottlenecks in the suction circuit. When a clog forms in the suction tubing, it is often difficult to dislodge the debris causing the clog. Thus, it is often necessary to stop the procedure, shut off the vacuum device, replace the tubing, then continue the procedure. This interruption can increase the labor hours required for certain procedures, and thus represents additional costs suffered by the medical facility in performing the medical procedure.

It has been found that the partially collapsed portions of conventional suction tubing contributes significantly to the clogging problem. Another aspect of at least one of the inventions disclosed herein includes the realization that where a larger diameter suction tubing is partially collapsed, the resulting cross sectional size of the collapsed portion can be large enough to reduce the likelihood of clogs from forming at the partially collapsed portion.

Thus, in accordance with yet another aspect of at least one of the inventions disclosed herein, a suction hose kit comprises a sterilized package enclosing tubing having an inner diameter of at least about 8 mm. As such, the tubing can be made from the typically-used soft plastic material and folded into a compact shape, without causing constrictions that cause the clogging problem associated with the conventional smaller diameter suction tubing. Other objects, advantages, and features of the present invention will become readily apparent to those skilled in this art from the ensuing detailed description of preferred embodiments thereof.

BRIEF DESCRIPTION OF THE DRAWINGS

FIG. 14 is a schematic elevational and sectional view of a suction jar commonly used for collecting fluids suctioned from a wound of a patient during an operation.

FIG. 15 is an enlarged side elevational view of a female adapter mounted to a suction hose commonly used in operating rooms.

FIG. 16 is a suction device commonly used in operating rooms and configured to engage with the female adapter illustrated in FIG. 15.

FIG. 17 is an exploded view of a sterilized package and a suction hose commonly used in operating rooms.

FIG. 18 is a sectional view of the suction hose illustrated in FIG. 17, taken along line 18-18.

FIG. 19 is a sectional view of the suction hose illustrated in FIG. 17, taken along line 19-19.

FIG. 20 is a sectional view of an improved suction hose constructed in accordance with an aspect of at least one of the inventions disclosed herein.

DETAILED DESCRIPTION OF THE PREFERRED EMBODIMENT

Figure 1:
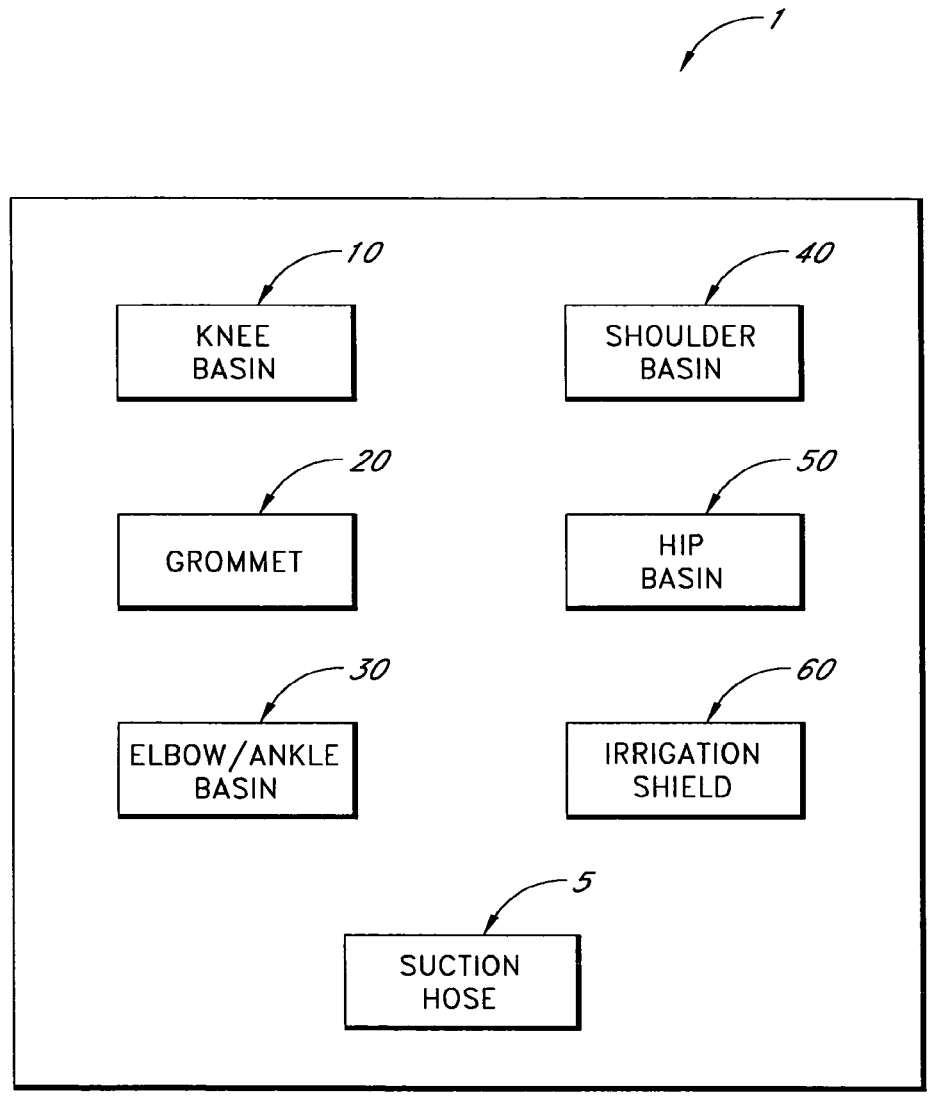
FIG. 1 is a block diagram of an irrigation kit.

With reference to FIG. 1, a block diagram of an irrigation kit 1 according to an embodiment of at least one of the inventions disclosed herein is illustrated therein. The irrigation kit 1 comprises a basin 10 for irrigation of a wound on a human knee, a grommet 20, a basin 30 for irrigation of a wound on a human elbow or ankle, a basin 40 for irrigation of a wound on a human shoulder, a basin 50 for irrigation of a wound on a human hip and an irrigation shield 60, each of which are described in greater detail below.

The kit 1 preferably also comprises a cover 2 that envelops the basins 10, 20, 30, 40, 50, the grommet 20 and the shield 60 together. The cover 2 is configured to form a seal over the kit 1 to maintain the contents of the kit 1 in a sterilized state. Additionally, the cover 2 is configured to be readily removed by a user for easy access to the contents of the kit 1.

The cover 2 is preferably made of a material that can maintain the contents of the kit 1 in a sterilized state. For example, the cover 2 may be made of plastic. Alternatively, the cover 2 may be made of reinforced paper or a cloth.

As discussed above, the kit 1 preferably comprises a plurality of basins, preferably one each of the basins 10, 30, 40, 50. However, the kit 1 can optionally include any number of each basin type. Additionally, the kit 1 preferably comprises an irrigation shield 60 and/or optionally, a grommet 20.

The kit 1 optionally comprises a cannula 5 configured to operate as a suction hose. The cannula 5 is preferably made of a flexible plastic. The cannula 5 can optionally be made of a hard plastic, such as, but not limited to, polyurethane or polypropylene. The cannula 5 can also comprise a variety of shapes, such as, but without limitation, a C-shape, a Z-shape, and an L-shape. At least one end of the cannula 5 is configured to engage a suction device.

The cannula 5 preferably comprises a cylindrical outer surface. However, the outer surface of the cannula 5 can comprise other shapes, such as, but without limitation, square and hexagonal.

Figure 1A:
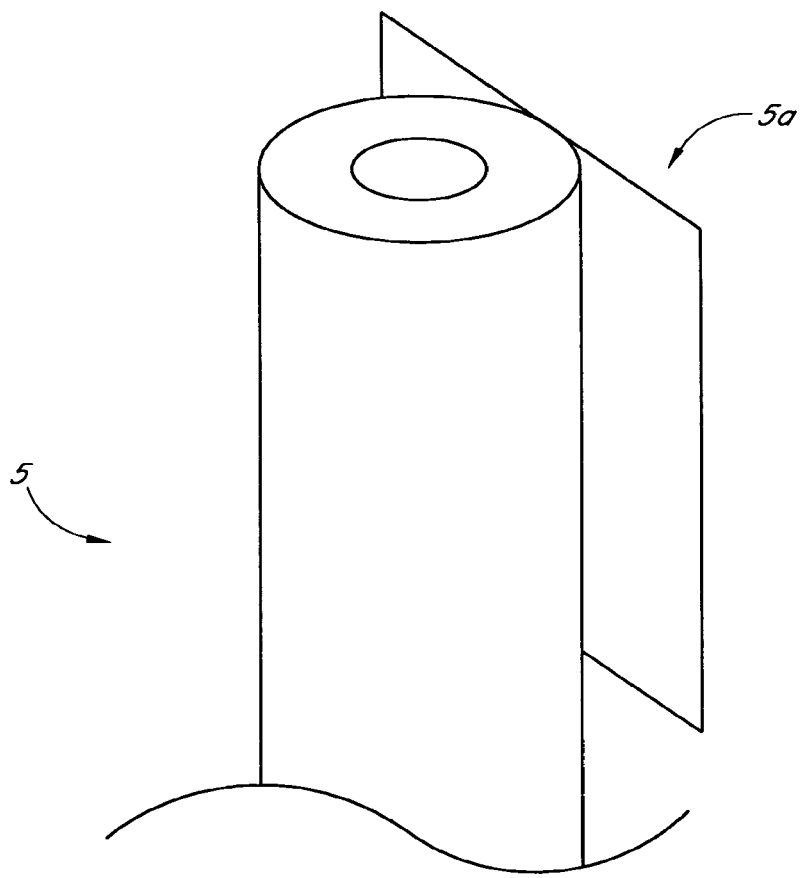
FIG. 1a is a perspective view of a cannula having an adhesive surface.

With reference to FIG. 1a, the cannula 5 also preferably comprises an adhesive surface 5a. For example, the adhesive surface 5a can comprise the outer surface of the cannula 5. In another example, the adhesive surface 5a can comprise a flange 5a integrally formed on an outer surface of the cannula 5. In another example, the flange 5a can be attached to the outer surface of the cannula 5 with, for example, but without limitation, an adhesive. The cannula 5 preferably comprises a peel-off cover over the adhesive surface 5a. The cannula 5 advantageously provides a simple attachment for use with any of the basins described above to actively drain said basin.

During use, the user takes a kit 1 from a storage location when needed for use in an irrigation procedure. The user removes the cover 2 of the kit 1 and removes its contents. The cover 2 may be removed by opening the seal of the cover 2. Alternatively, the cover 2 may be removed by cutting the material of the cover 2 with a sharp instrument, such as a knife, scalpel, or scissors.

Figure 2:
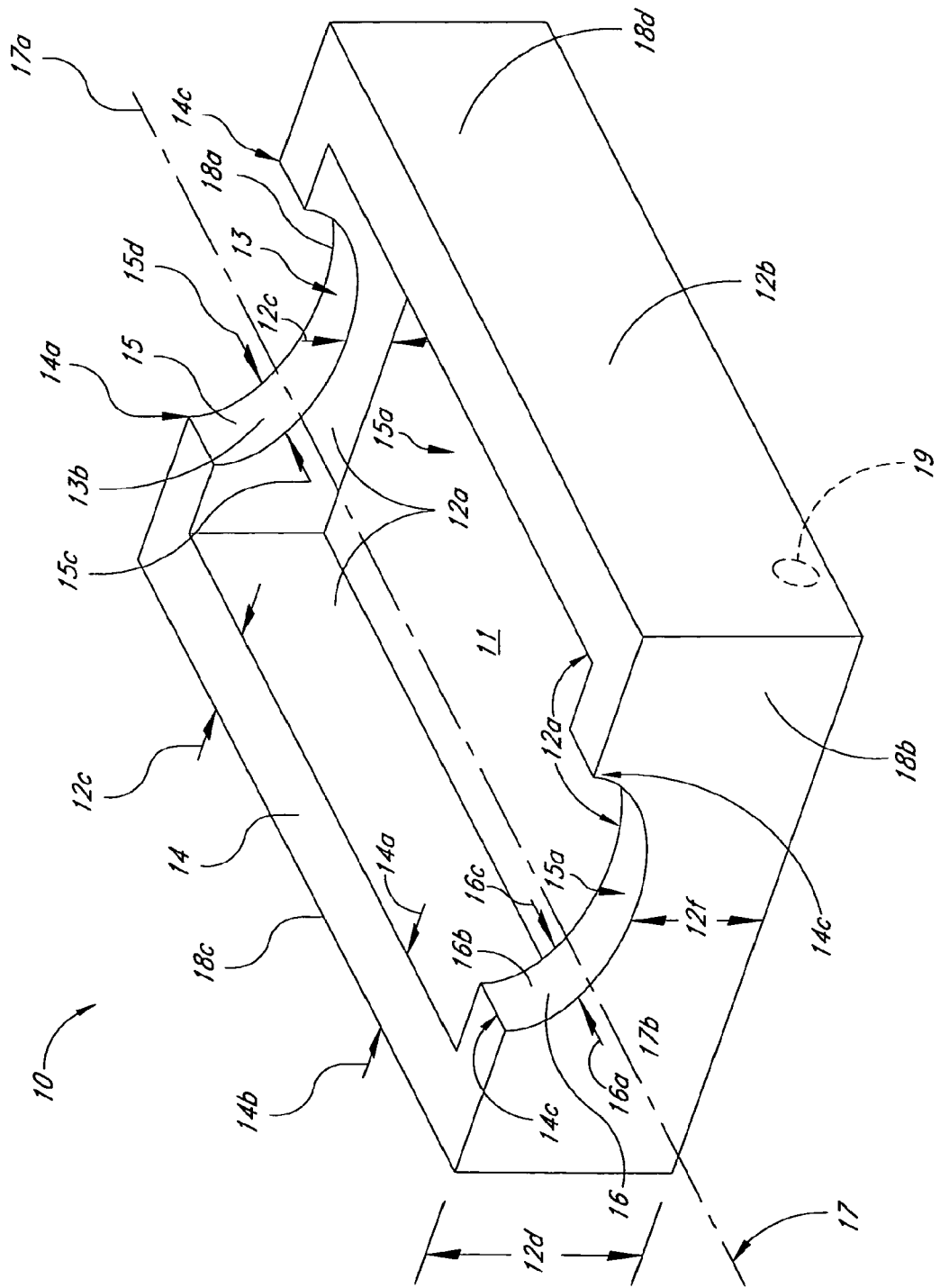
FIG. 2 is a perspective view of an irrigation basin for irrigating a wound on a human extremity having a frangible portion.

With reference to FIG. 2, an irrigation basin 10 for irrigating a wound on a human extremity is illustrated therein. For example, the basin 10 can be used for irrigating a wound on a human knee. The basin 10 comprises a base 11 having a generally rectangular shape and a peripheral wall 12. The basin 10 can have other shapes, such as, but without limitation, round, oval, kidney, and square. The wall 12 is substantially at ninety degrees relative to a resting surface upon which the basin 10 rests. However, the wall 12 can be inclined at any desired angle, inwardly or outwardly.

The base 11 and the wall 12 define a cavity 13 in the center of the basin 10. The peripheral wall 12 also defines an inner surface 12a facing toward the cavity 13 of the basin 10 and an outer surface 12b facing away from the cavity 13 of the basin 10. The basin 10 also comprises an upper periphery 14 having an inner edge 14a and an outer edge 14b. The outer edge 14b preferably joins the upper periphery 14 to the outer surface 12b. In the illustrated embodiment, the periphery 14 defines an inwardly extending flange having a width 12c, supported only by the connection between the outer edge 14b to the wall 12. Optionally, the flange can extend outwardly from the wall 12. Alternatively, the thickness of the wall 12 can be sufficient to form the periphery 14. In another option, the inner edge 14a joins the upper periphery 14 to the outer surface 12b and the periphery 14 is supported only by the connection between the inner edge 14a to the wall 12.

The basin 10 is preferably made of a hard plastic material. For example, but without limitation, the basin 10 can be made of polyurethane or polypropylene, among other materials. The material is preferably biocompatible and hypo-allergenic. The basin 10 can also be made of metal, such as, but without limitation, stainless steel. Additionally, the basin 10 is preferably sterilized for use in medical procedures. The basin 10 can optionally be re-useable.

The outer surface 12b comprises two end surfaces 18a, 18b arranged at longitudinal ends 17a, 17b of a major axis 17, respectively, and disposed generally perpendicular to the major axis 17. The outer surface 12b also comprises two side surfaces 18c, 18d extending between the longitudinal ends 17a, 17b and generally parallel to the major axis 17. As used herein, the term "major axis" generally refers to an axis that passes through the basin 10 along the longitudinal direction of the basin 10, i.e., along the greatest dimension or "length" of the basin 10.

The basin 10 further comprises a first recess 15 configured to receive, for example, a human thigh and a second recess 16 configured to receive, for example, a human shin. The first recess 15 is preferably broader than the second recess 16. The first recess 15 is disposed along the upper periphery 14 at the longitudinal end 17a of the basin 10. The recess 15 bisects the end surface 18a and the inner surface 12a at the longitudinal end 17a.

The second recess 16 is disposed along the upper periphery 14 at the longitudinal end 17b of the basin 10. The recess 16 bisects the end surface 18b and the inner surface 12a at the longitudinal end 17b. The recesses 15, 16 are preferably aligned along the axis 17.

Figure 2A:
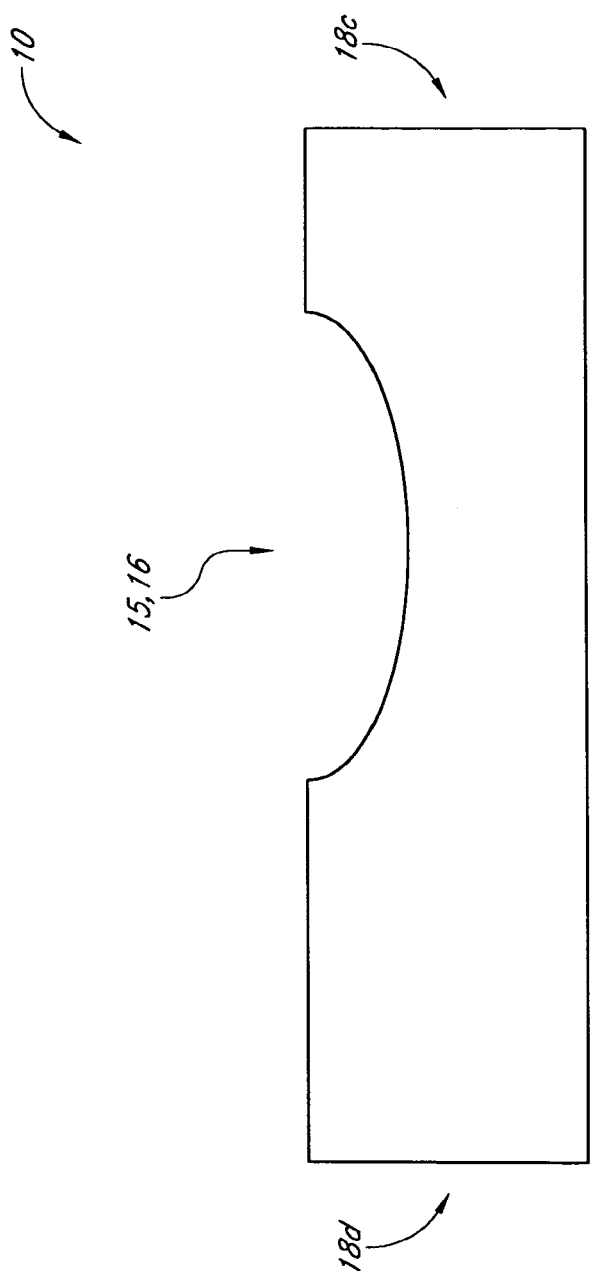
FIG. 2a is an end view of the irrigation basin in FIG. 2 having recesses proximally disposed to the sidewalls.

FIG. 2 illustrates the recesses 15, 16 as centrally disposed along the upper periphery 14 at the longitudinal ends 17a, 17b of the basin 10. However, as illustrated in FIG. 2a, the recesses 15,16 can optionally be disposed along the periphery 14 proximally to one of the side surfaces 18c, 18d. The recesses 15, 16 preferably join to the upper periphery 14 at edges 14c.

The basin 10 also optionally includes at least one convertible portion 19 communicating with an area near the bottom edge of the basin 10, where the bottom edge is the edge that contacts the resting surface. One convertible portion 19 is shown in the illustrated embodiment. The convertible portion 19 can optionally be disposed on the base 11. In one example, the convertible portion 19 can be centrally disposed on the bottom of the base 11. In the illustrated embodiment, the convertible portion 19 is disposed on the side surface 18d.

As shown in FIG. 2, the base 11 of the basin 10 is generally horizontal relative to the resting surface and rectangular in shape. Moreover, the base 11 is substantially at zero degrees relative to the resting surface. However, the base 11 of the basin 10 is not limited to the rectangular shape or to being parallel to the resting surface. For example, the base 11 may be inclined at an angle greater than zero degrees and configured to direct irrigation fluid on the base 11 in the direction of the convertible portion 19. For example, the wall 12 can include downwardly protruding portions (not shown) which raise the end 17a relative to the end 17b. Alternatively, the base 11 can be mounted to the wall 12 such that the end of the base 11 adjacent end 17a is higher than the end of the base 11 adjacent the end 17b. In another example, the base 11 can be configured to be adjustably inclined to a plurality of angles such that the end of the base 11 adjacent end 17a is higher than the end of the base 11 adjacent the end 17b. For example, but without limitation, the outer surface of the base 11 can be configured to releasably engage at least one shim (not shown) to selectively change the inclination of the base 11 relative to the resting surface. Thus, the kit 1 can include a basin 10 and at least one shim to selectively vary the inclination of the base 11.

The peripheral wall 12 defines a thickness, which preferably is uniform along the periphery of the wall 12. The thickness is configured to provide the wall 12 with adequate structural rigidity to prevent excessive flexing of the wall 12. Accordingly, the thickness can optionally have various sizes, each of which is capable of providing the wall 12 with adequate structural rigidity. For example, the thickness can be between 1 mm and 5 cm.

The wall 12 defines a maximum height 12d along the periphery of the wall 12. The maximum height 12d is defined as the distance from the resting surface to the upper periphery 14 of the wall 12. The wall 12 also defines a minimum height 12e at the longitudinal end 17a of the basin. The minimum height 12e is defined as the distance from the resting surface to a minimum point 15a of the first recess 15. Further, the wall defines a minimum height 12f at the longitudinal end 17b of the basin 10. The minimum height 12f is defined as the distance from the resting surface to a minimum point 16a of the second recess 16. The heights 12d, 12e, 12f are configured to be sufficiently large to allow the cavity 13 defined by the wall 12 and the base 11 to hold a substantial volume of fluid.

The upper periphery 14 in the illustrated embodiment is generally parallel to the axis 17. However, the upper periphery 14 can optionally be inclined inwardly so as to drain liquid falling on the periphery 14 back into the cavity 13. Additionally, the periphery 14 can have a curved surface so that the periphery 14 does not have the edges 14a, 14b and to provide a seamless junction between the upper periphery 14 and the outer surface 12b.

The first recess 15, as illustrated in FIG. 2, extends from the edges 14c of the upper periphery 14 to the minimum point 15a. Moreover, the recess 15 has a curved shape. However, the first recess 15 can optionally have any contoured shape configured to receive, for example, a human thigh. Accordingly, the recess 15 is not limited to the arcuate shape illustrated in FIG. 2. The recess 15 further comprises a recess surface 15b and edges 15c, 15d. The recess 15 preferably joins to the wall 12 at the edge 15d. Optionally, the recess 15 can join to the wall 12 at the edge 15c. The recess surface 15b extends horizontally from the edge 15c to the edge 15d adjacent the end surface 18a. The recess surface 15b can optionally be curved between the inner surface 12a and the end surface 18a to provide a seamless junction between the surface 15b and the surfaces 12a, 18a without the edges 15c, 15d. The recess surface 15b can also optionally be inclined inwardly so as to drain liquid falling on the surface 15b back into the cavity 13. The first recess 15 may also have a contoured juncture with the upper periphery 14 to provide a seamless junction between the recess surface 15b and the upper periphery 14, without the edges 14c.

Similarly, the second recess 16 has a generally curved shape, as illustrated in FIG. 2, and extends from the edges 14c of the upper periphery 14 to the minimum point 16a. Moreover, the second recess 16 has a curved shape, which can be different than the curved shape of the first recess 15. Accordingly, the first recess 15 and the second recess 16 can optionally be asymmetric. Additionally, the second recess 16 can optionally have any contoured shape configured to receive, for example, a human shin. Therefore, the recess 16 is not limited to the arcuate shape illustrated in FIG. 2. The recess 16 further comprises a recess surface 16b and edges 16c, 16d. The recess 16 preferably joins to the wall 12 at the edge 16d. Optionally, the recess 16 can join to the wall 12 at the edge 16c. The recess surface 16b extends horizontally from the edge 16c to the edge 16d adjacent the end surface 18b. The recess surface 16b can optionally be curved between the inner surface 12a and the end surface 18b to provide a seamless junction between the surface 16b and the surfaces 12a, 18b without the edges 16c, 16d. The recess surface 16b can also optionally be inclined inwardly so as to drain liquid falling on the surface 16b back into the cavity 13. The second recess 16 may also have a contoured juncture with the upper periphery 14 to provide a seamless junction between the recess surface 16b and the upper periphery 14, without the edges 14c.

The convertible portion 19 can comprise a variety of structures and combination of structures. Moreover, as noted above, one or a plurality of convertible portions 19 can be disposed along the periphery of the basin 10 or on the base 11.

Figure 2B:
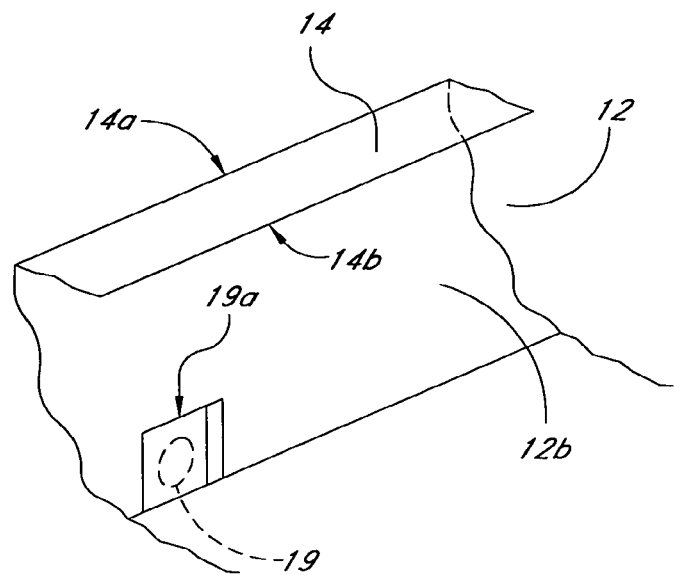
FIG. 2b is an enlarged perspective view of an irrigation basin with a hole and a peel-off seal.

For example, but without limitation, the convertible portion 19 can comprise a hole 19 formed on the base 11 or the wall 12 covered with a peel-off seal 19a, as illustrated in FIG. 2b. The peel-off seal 19a can be disposed on the inner surface 12a or the outer surface 12b of the basin 10, or on the bottom of the base 11. Preferably, the seal 19a is constructed of an adhesive applied to a thin light-weight plastic, such as, for example, but without limitation, a thermo-plastic. The adhesive is configured to allow the thin plastic portion to be peeled-off of the basin 10 by hand.

The basin 10 can optionally comprise a strainer portion (not shown) over the hole 19, where the strainer is configured to capture bone chips, soft tissue, and other debris. The peel-off seal 19a advantageously provides a simple way of creating a drain on the basin 10 or any container used for collecting contaminated and potentially infectious fluids, such as, but without limitation, bed pans.

A kit 1 including the basin 10 can also comprise additional peel-off seals 19a configured to cover the hole 19. The additional peel-off seals 19a can be used to cover the hole 19 if a drain is no longer desired.

Figure 2C:
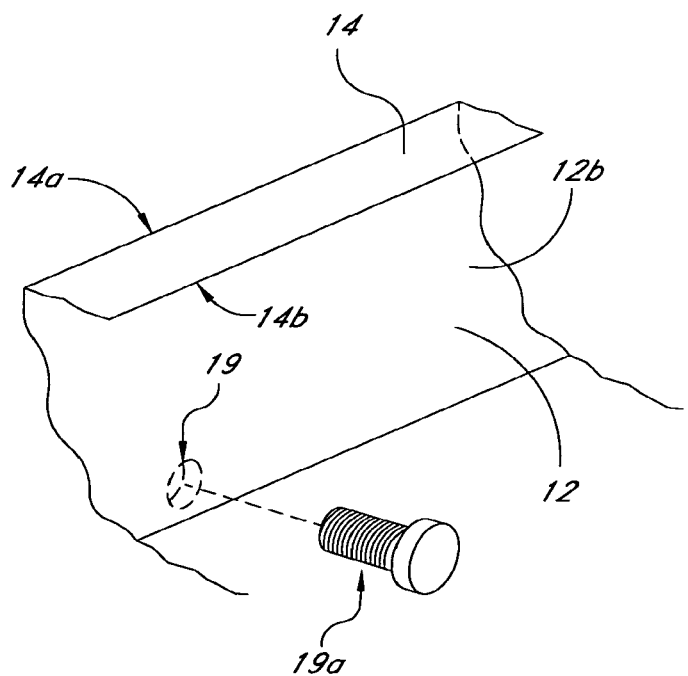
FIG. 2c is an enlarged perspective view of an irrigation basin with a threaded hole and a threaded plug.

In another example, the convertible portion 19 can comprise a threaded hole 19 formed on the wall 12 and a threaded plug 19a to plug the hole 19, as illustrated in FIG. 2c. The plug 19a and threaded hole 19 advantageously allow medical personnel to readily modify the convertible portion 19 to create a drain in the basin 10 by removing the plug 19a from the hole 19. Similarly, personnel can insert the plug 19a into the hole 19 if a drain is no longer desired. The threaded hole 19 and threaded plug 19a advantageously provide a simple way of creating a drain on the basin 10 or any container used for collecting contaminated and potentially infectious fluids, such as, but without limitation, bed pans.

Figure 2D:
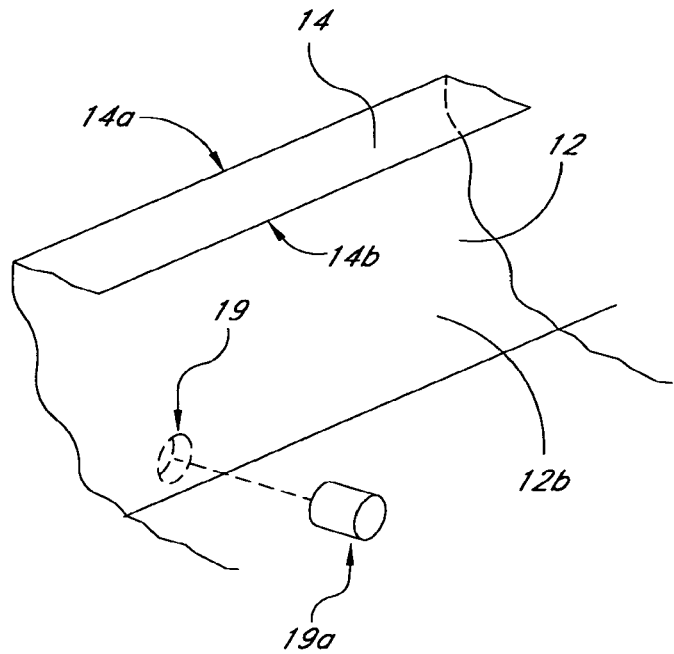
FIG. 2d is an enlarged perspective view of an irrigation basin with a hole and a removable cork.

In still another example, the convertible portion 19 can comprise a hole 19 formed on the wall 12 and a removable cork 19a to cover the hole 19, as illustrated in FIG. 2d. The cork 19a advantageously allows medical personnel to readily modify the convertible portion 19 to create a drain in the basin 10 by removing the cork 19a from the hole 19. Similarly, personnel can insert the cork 19a into the hole 19 if a drain is no longer desired. The hole 19 and removable cork 19a advantageously provide a simple way of creating a drain on the basin 10 or any container used for collecting contaminated and potentially infectious fluids, such as, but without limitation, bed pans.

Figure 2E:
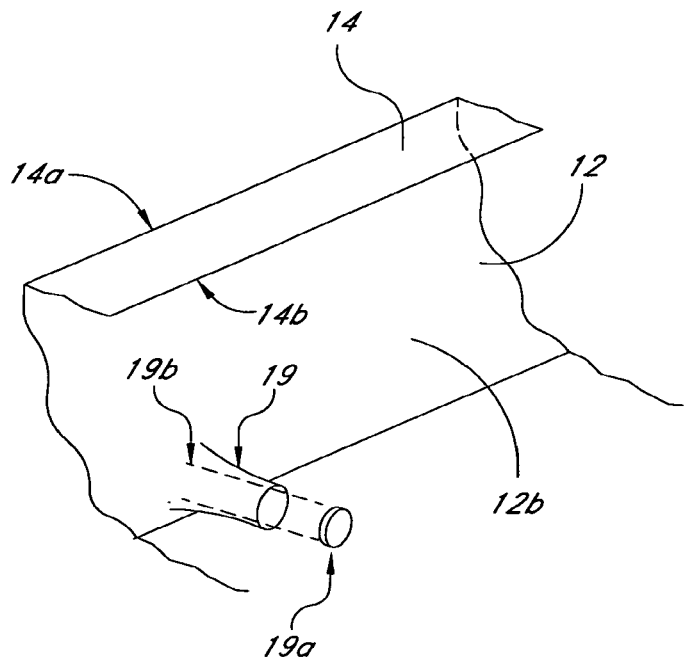
FIG. 2e is an enlarged perspective view of an irrigation basin with a nipple and a removable cap.

In yet another example, the convertible portion 19 can comprise a nipple 19 extending outward from the side surface 18d having a removable cap 19a, as illustrated in FIG. 2e. The nipple 19 can be molded onto the side surface 18d. Optionally, the nipple 19 can be removably screwed onto a threaded hole on the side surface 18d. The nipple 19 defines a channel 19b extending therethrough to the inner surface 12a of the basin 10. The nipple 19 and cap 19a advantageously provides a way to create a drain in the basin 10 by removing the cap 19a from the nipple 19, which allows fluid in the basin 10 to flow through the channel 19b of the nipple 19. Similarly, medical personnel can place the cap 19a over the nipple 19 if a drain is no longer desired. The nipple 19 and removable cap 19a advantageously provide a simple way of creating a drain on the basin 10 or any container used for collecting contaminated and potentially infectious fluids, such as, but without limitation, bed pans.

Figure 2F:
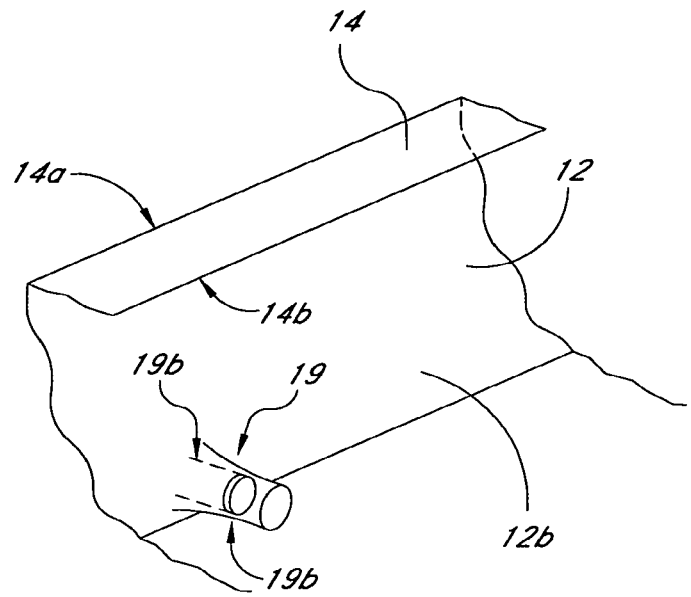
FIG. 2f is an enlarged perspective view of an irrigation basin with a nipple and a peel-off seal.

In another example, the convertible portion 19 can comprise a nipple 19 having a strainer (not shown) and a removable cover 19a, such as, but not limited to, a peel-off seal 19a, as illustrated in FIG. 2f. As discussed above, the nipple 19 defines a channel 19b extending therethrough to the inner surface 12a. The peel-off seal 19a is preferably disposed over the protruding nipple 19. Alternatively, the peel-off seal 19a can be disposed on the inner surface 12a over the strainer. This configuration advantageously provides a convertible portion 19 that is readily modifiable to create a drain in the basin 10 by peeling off the peel-off seal 19a, and that captures soft tissue, bone chips, and other debris during the draining of the basin 10. The basin 10 can also comprise additional peel-off seals 19a configured to cover the nipple 19. The nipple 19 and peel-off seal 19a advantageously provide a simple way of creating a drain on the basin 10 or any container used for collecting contaminated and potentially infectious fluids, such as, but without limitation, bed pans.

Figure 2G:
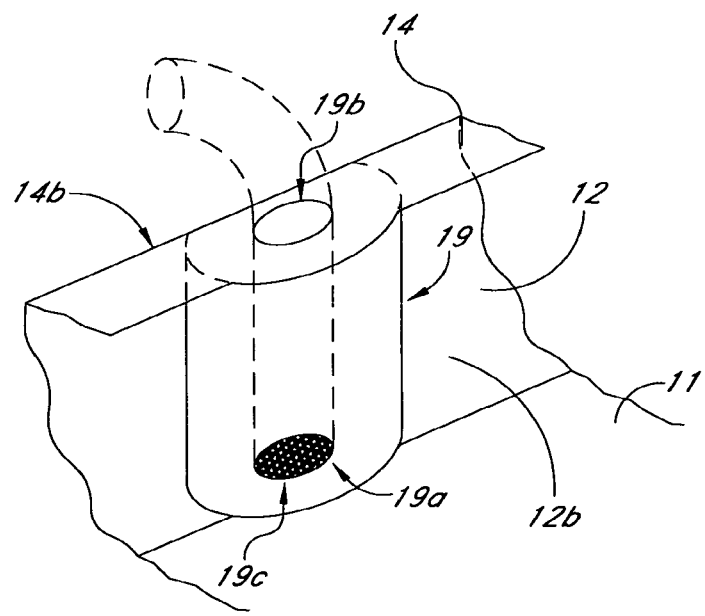
FIG. 2g is an enlarged perspective view of an irrigation basin with a cannula.

In still another example, the convertible portion 19 can comprise a cannula 19 extending generally vertical to the resting surface from an aperture 19a proximal to the base 11 to an aperture 19b proximal to and disposed on a plane generally parallel to the periphery 14, as illustrated in FIG. 2g. However, the cannula 19 can optionally extend above the periphery 14, as shown in phantom in FIG. 2g.

The cannula 19 can optionally be integrally molded to the inner surface 12a of the basin 10. In another option, the cannula 19 can optionally be integrally molded to the outer surface 12b of the basin 10 and extend through the wall 12 such that the aperture 19a is disposed generally along the base 11. In still another option, the aperture 19b of the cannula 19 can face away from the basin 10. In yet another option, the cannula 19 can be removably attached to the inner surface 12a of the basin 10.

The aperture 19a proximal to the base 11 optionally comprises a perforated screen 19c to prevent bone chips, soft tissue, and other debris from entering the cannula. A peel-off seal (not shown) can optionally be disposed over the perforated screen 19c. The aperture 19b proximal to the periphery 14 is configured to receive a fitting to actively drain the basin 10. Optionally, the aperture 19b proximal to the periphery can receive and hold a flexible tube to actively drain the basin 10. As another option, the portion of the cannula 19 proximal to the periphery 14 includes a nipple (not shown) sized to fit within a suction hose commonly used in operating rooms.

Figure 2H:
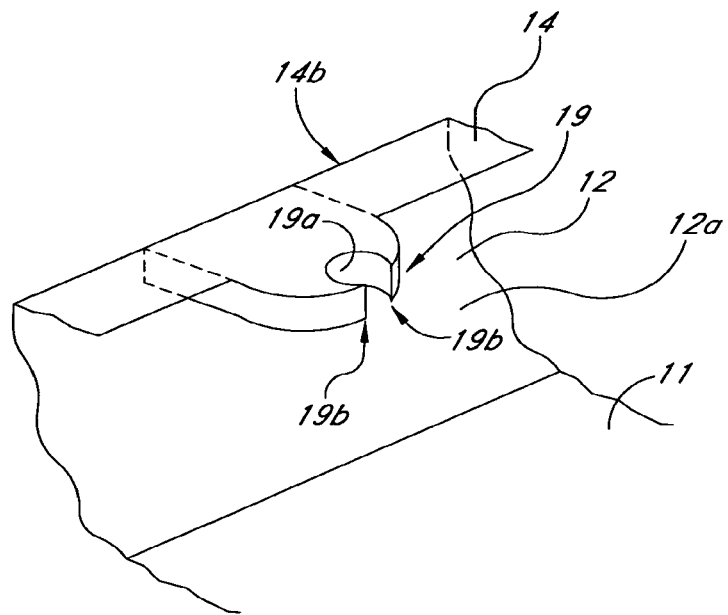
FIG. 2h is an enlarged perspective view of an irrigation basin with a clamp.

In yet another example, the convertible portion 19 can comprise a clamp 19, as illustrated in FIG. 2h. The clamp 19 can optionally be integrally molded to the inner surface 12a of the basin 10. In another option, the clamp 19 can be removably attached to the inner surface 12a of the basin 10. The clamp 19 comprises a contact surface 19a defined by two arms 19b about an axis. The contact surface 19a is configured to receive a tube, but allow said tube to be adjusted along said axis in response to a force. The arms 19b are configured to hold the tube against the contact surface 19a. The clamp 19 advantageously provides a simple structure on the basin 10 that can be used in conjunction with a tube or a fitting to actively drain the basin 10. Moreover, the tube can advantageously be adjusted while the arms 19b of the clamp 19 hold it. Medical personnel can thus adjust the tube to a position that provides the best active draining of the basin 10.

Figure 2I:
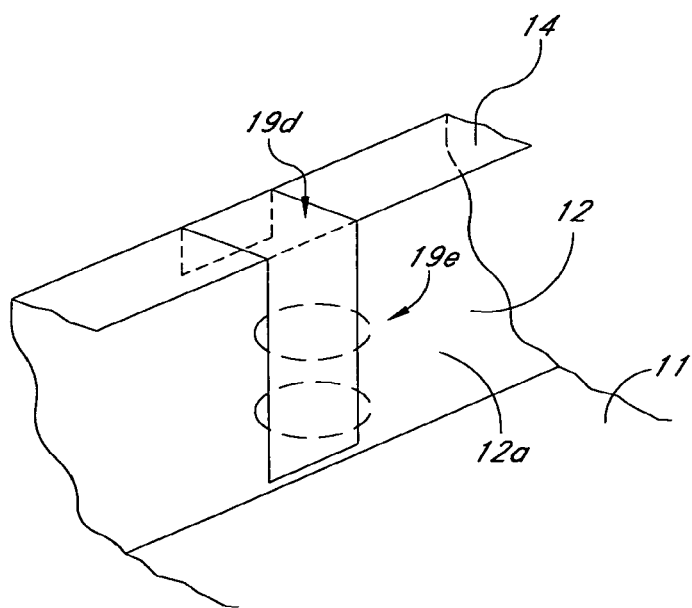
FIG. 2i is an enlarged perspective view of an irrigation basin with a removable clip holder.

In another example, the convertible portion 19 can comprise a removable holder 19d having at least one clip 19e, as shown in FIG. 2i. Two clips 19e are shown in the illustrated embodiment. The clips 19e are configured to engage and hold a conventional suction hose against the holder 19d and proximal to the base 11 of the basin 10 for active draining of the basin 10. The clips 19e are optionally manually actuated to engage the suction hose. Similarly, the clips 19e are optionally manually actuated to release the hose when active draining is no longer desired. The holder 19d is configured to fit over the periphery 14 of the basin 10 such that it hangs generally vertical to the resting surface. Thus, a kit 1 including an irrigation basin 10 can include a removable holder 19d having at least one clip 19e to allow the basin 10 to be readily converted for draining.

Figure 2J:
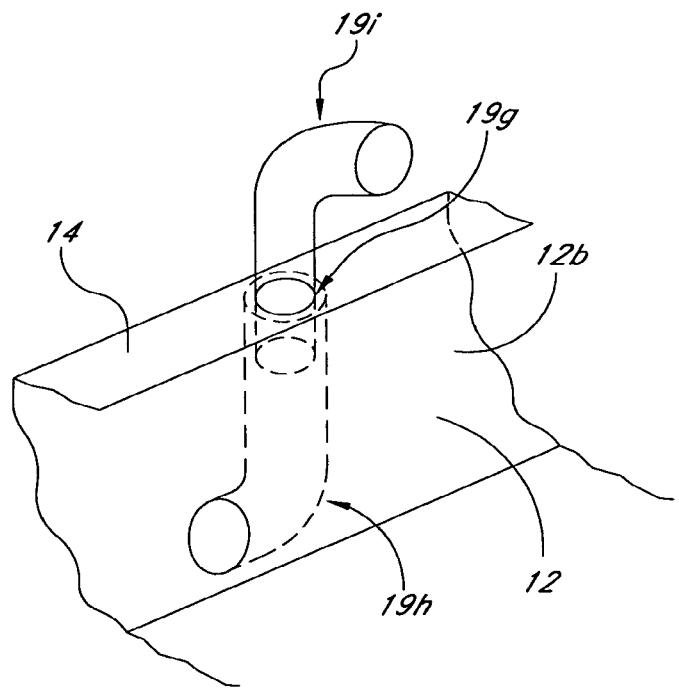
FIG. 2j is an enlarged perspective view of an irrigation basin having an aperture along the upper periphery and two cannulas.

In still another example, the convertible portion 19 can comprise an aperture 19g formed on the upper periphery 14 of the basin 10, as illustrated in FIG. 2j. The aperture 19g is configured to align with a first cannula 19h disposed under the periphery 14 such that an upper end of the first cannula 19h abuts against an underside of the periphery 14 about the aperture 19g. The first cannula 19h preferably has an outer diameter that is greater than the diameter of the aperture 19g. The upper end of the first cannula 19h is configured to receive a lower end of a second cannula 19i that is inserted through the aperture 19g and through the upper end of the first cannula 19h. The second cannula 19i preferably has an outer diameter that is smaller than an inner diameter of the first cannula 19h. The cannulas 19h, 19i are preferably made of a hard plastic. Optionally, the cannulas 19h, 19i can be made of a flexible rubber.

With reference to 2k in yet another modification, the convertible portion 19 can comprise a recess 19j defined on the inner surface 12a of the wall 12. The recess 19j preferably is configured to releasably engage a suction hose that is commonly used in an operating room or medical facility. For example, the Sherwood Medical Company of St. Louis, Mo. manufacturers suction hose under the trade name "Argyle® non-conductive connecting tube with shore group female molded connectors". The Argyle® suction hose has an inner diameter of about 6 millimeters and an outer diameter of about 9 millimeters. Thus, the recess 19j preferably is configured to releasably engage a hose having an outer diameter of about 9 millimeters with an interference fit.

Figure 2K:
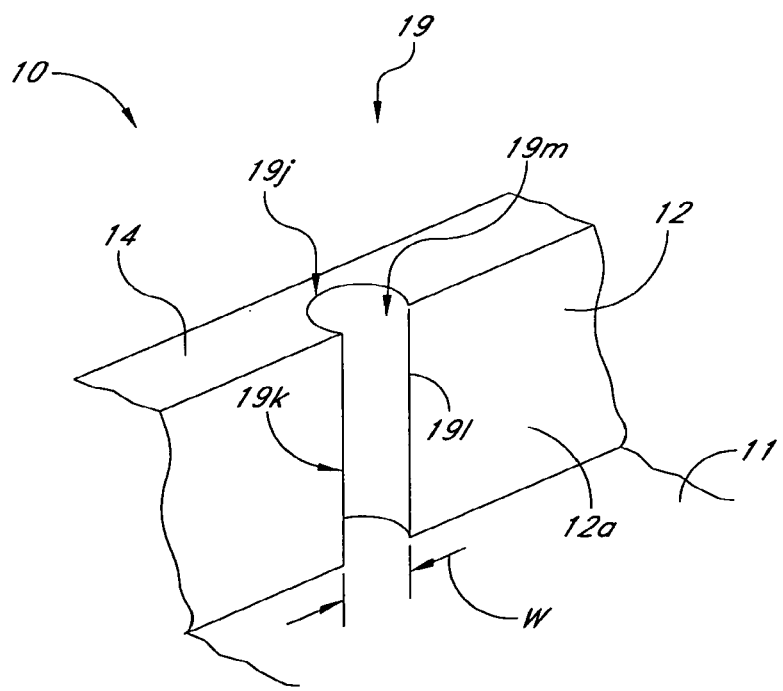
FIG. 2k is an enlarged perspective view of an irrigation basin with a recess configured to engage a suction hose.

For example, the recess 19j can include lateral edges 19k, 19l. A rear wall 19m can connect the lateral edges 19k, 19l. Preferably, the spacing W between the lateral edges 19k, 19l is less than about 9 millimeters. Optionally, the lateral edges 19k, 19l can include tabs (not shown) extending from the lateral edges 19k, 19l, thereby further reducing the minimum clearance between the lateral edges 19k, 19l. Thus, the standard Argyle® suction hose can be snapped into the recess 19j. Further, the lateral edges 19k, 19l and rear wall 19m are sized so as to provide an interference fit with the outer surface of suction hose, such as the Argyle® 6 millimeter suction hose, or any other suction hose. Thus, once the suction hose is snapped into the recess 19j, the hose is held in place through an interference fit therewith. As such, the basin 10 illustrated in FIG. 2k can be quickly and conveniently modified by attaching a commonly used suction hose to the convertible portion 19.

Optionally, a strainer (not shown) can be attached to the lower end of the suction hose to be connected to the convertible portion 19. Thus, the strainer can prevent large clumps of tissue and bone fragments from entering the suction hose, so as to reduce the likelihood of clogging.

According to the illustrated embodiment of the basin 10, the at least one convertible portion 19 is in the form of an annularly extending score 19 defining a frangible portion disposed on the side surface 18d. However, the score 19 can be disposed on any portion of the wall 12 or the base 11. Additionally, a plurality of scores 19 can optionally be disposed on the basin 10. The score 19 is configured to form an aperture through the wall 12 or base 11 to drain the cavity 13 following the removal of the material bounded by the score 19 from the wall 12. The score 19 is preferably disposed near the bottom of the surface 18d, close to the resting surface. However, the score 19 can be disposed in any location capable of providing an effective drain for the cavity 13 upon the removal of the material bounded by the score 19 from the wall 12. Additionally, though the score 19 preferably comprises a circular shape, as shown in the illustrated embodiment, the score 19 can comprise any shape that provides an effective drain for the cavity 13. For example, the score 19 can comprise a slit.

In preparation for the irrigation of a knee wound, medical personnel remove the cover 2 from the kit 1 and remove the basin 10 from the kit. If the wound is in the knee area along the front part of the leg, personnel have the patient sit on an examination table with their leg extended. The patient can optionally lie on his or her back if the wound is on the back of the knee. Medical personnel then place the basin 10 under the extended leg of the patient so that the patient's thigh rests on the first recess 15 and the patient's shin rests on the second recess 16. Accordingly, the patient's wound is disposed over the cavity 13 of the basin 10. If the wound is in the knee area along the back part of the leg, personnel have the patient lay on their stomach with their injured leg extended. The personnel then place the basin 10 under the patient's leg as described above. If the personnel wish to actively drain the basin 10 during the irrigation procedure, the personnel modify the convertible portion 19. As noted above, the basin 10 can comprise a plurality of convertible portions 19 disposed along the periphery of the basin 10, allowing personnel to choose the convertible portion 19 that best accommodates the draining of the basin 10 or create additional drains. The draining device and active draining process are further described below.

If the convertible portion 19 comprises a hole 19 formed on the wall 12 covered with a removable cover, such as a peel-off seal, a threaded plug, and a cork, one can modify the convertible portion 19 by removing the cover from the hole 19. This allows irrigation fluid in the cavity 13 of the basin 10 to flow out of the basin through the hole 19.

In another example, if the convertible portion 19 comprises a nipple 19 having a removable cap 19a, personnel can modify the convertible portion 19 by removing the cap 19a from the nipple 19. In still another example, if the convertible portion 19 comprises a nipple 19 having a strainer and a peel-off seal 19a, personnel can modify the convertible portion 19 by peeling off the seal 19a. Personnel can then connect a suction hose to the nipple and connect the suction hose to a suction device to actively drain the basin 10.

In yet another example, if the convertible portion 19 comprises a cannula 19, personnel can insert a conventional tube into the cannula 19. Personnel can then connect an end of the suction tube to a suction device to actively drain the basin 10.

In another example, if the convertible portion 19 comprises a clamp 19, medical personnel can attach a conventional suction hose to the clamp 19 so that an end of the suction hose is proximal to the base 11. Personnel can then connect a second end of the hose to a suction device to actively drain the basin 10.

In still another example, if the convertible portion 19 comprises a removable holder 19d with at least one clip 19e, medical personnel can attach the at least one clip 19e to a conventional suction hose so that an end of the suction hose is proximal to the base 11. Personnel can then connect a second end of the hose to a suction device to actively drain the basin 10.

In another example, if the convertible portion 19 comprises an aperture 19g formed on the upper periphery 14, personnel can place a first cannula 19h under the upper periphery 14 so that it aligns with the aperture 19g. Personnel can then insert a second cannula 19i through the aperture 19g and the first cannula 19h. Personnel can then connect a second end of the second cannula 19i to a suction hose or a suction device to actively drain the basin 10.

In yet another example, personnel can attach the adhesive surface 5a of the cannula 5 to the inner surface 12a of the basin 10 so that one end of the cannula 5 is proximal to the base 11 and the other end of the cannula 5 engages a suction device. In another option, the cannula 5 is configured to self-support against the inner surface 12a of the basin 10 without the adhesive surface 5a. The suction device can then be operated to actively drain the basin 10.

In the illustrated embodiment, where the convertible portion 19 comprises a frangible portion 19, personnel can break the frangible portion 19 to create a drain for the basin 10. Personnel can optionally insert a draining device into the drain and attach a suction hose to an end of the draining device. Personnel can then attach a second end of the suction hose to a suction device to actively drain the basin 10.

Irrigation fluid is then directed to the wound region to remove any contaminants from the wound region. The irrigation fluid directed to the wound region subsequently collects in the cavity 13 of the basin 10. The recesses 15, 16 that receive the thigh and shin of the patient, respectively, further improve the fluid-collection ability of the cavity 13 by reducing escape of irrigation fluid through the juncture of the thigh and shin with the recesses 15, 16, respectively.

Figure 3:
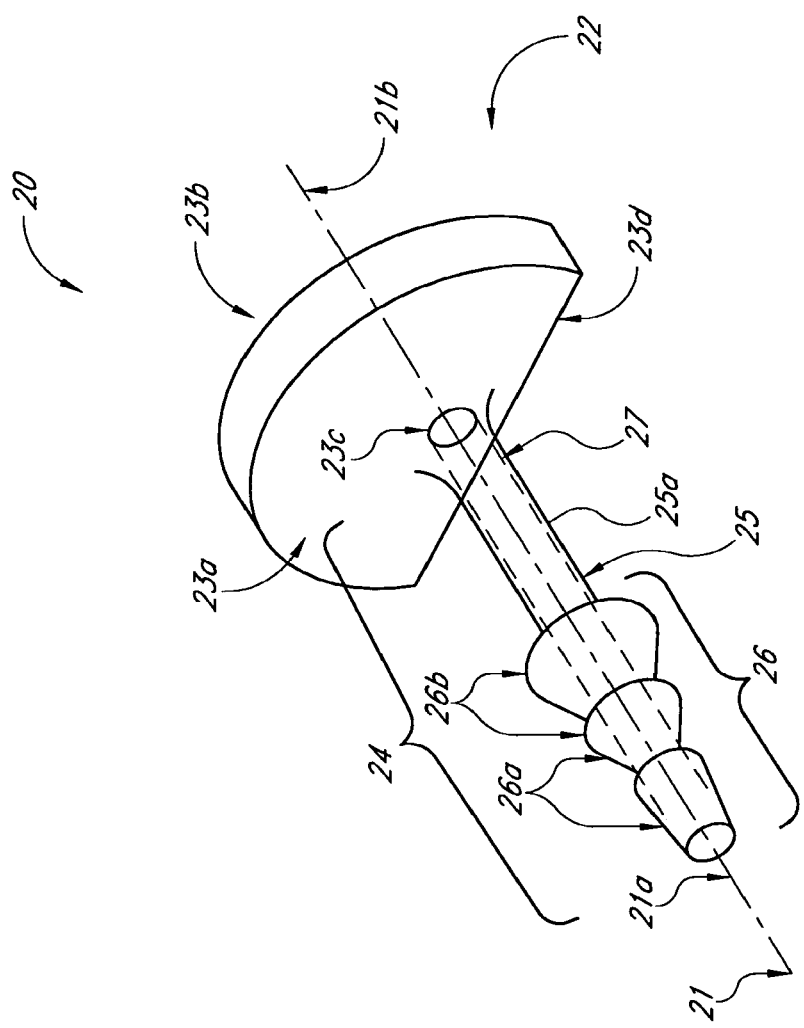
FIG. 3 is a front, top, and left side perspective view of a draining attachment for use with an irrigation basin.

With reference to FIG. 3, the draining device is illustrated therein. In the illustrated embodiment, the draining device is a grommet 20. The grommet 20 can optionally comprise a peel-off seal (not shown). The grommet 20 can also optionally comprise a strainer (not shown). In the illustrated embodiment, the grommet 20 defines an axis 21 along the longitude of the grommet 20, the axis 21 having two longitudinal ends 21a, 21b. The grommet 20 comprises a sealing part 22 and a fitting part 24. The grommet 20 is preferably made of a rigid material. For example, the grommet 20 can be made of a hard plastic. Optionally, the sealing part 22 and the fitting part 24 can be made of different materials. For example, the sealing part 22 can be made of a flexible rubber and the fitting part 24 can be made of a hard plastic.

The sealing part 22 is disposed at the longitudinal end 21b and comprises a sealing surface 23a facing in the direction of the longitudinal end 21a. The sealing surface 23a is configured to provide a substantially watertight seal with a mating surface (not shown) in contact with the sealing surface 23a. The sealing part 22 also comprises a drain surface 23b facing in the direction away from the longitudinal end 21a. The drain surface 23b defines a drain aperture 23c preferably disposed in a substantially central position on the drain surface 23b. Both surfaces 23a, 23b extend about the axis 21. The sealing part also comprises a bottom surface 23d proximal to the drain aperture 23c. The bottom surface 23d is preferably a flat surface.

Figure 3A:
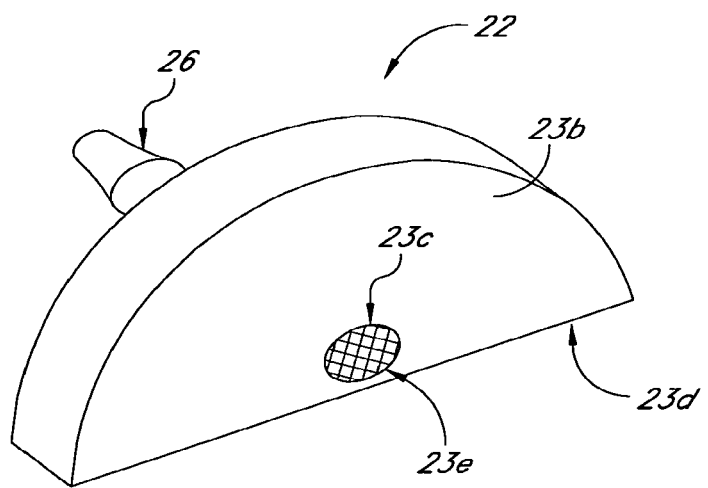
FIG. 3a is a rear, top, and left side perspective view of a draining attachment having an aperture with a strainer.

As illustrated in FIG. 3a, the grommet 20 optionally comprises a strainer 23e disposed on the drain surface 23b over the drain aperture 23c. The strainer 23e is configured to advantageously capture any bone debris, soft tissue, and other debris.

The fitting part 24 comprises a stem 25 having an outer surface 25a extending circumferentially about the axis 21. The fitting part 24 further comprises a plurality of steps 26 along the outer surface 25a of the stem 25, proximal to the longitudinal end 21a. In the illustrated embodiment, the fitting part 24 of the grommet 20 has three steps 26.

The plurality of steps 26 is configured to engage a tube disposed over the stem 25 at the longitudinal end 21a. For example, the steps 26 can be sized to elastically deform and thereby engage and seal against the inner surface of a suction hose commonly used in an operating room. The steps 26 comprise a running surface 26a and a stepping surface 26b, where both surfaces 26a, 26b extend circumferentially about the axis 21. The running surface 26a is preferably angled downward, relative to the axis 21, in the direction of the longitudinal end 21a. The running surface 26a of the plurality of steps 26 preferably has the same angle relative to the axis 21 for each of the steps 26. Optionally, the running surface 26a has a different angle relative to the axis 21 for each of the steps 26, the angle increasing with each of the steps 26 in a direction away from the longitudinal end 21a. The stepping surface 26b is preferably at substantially a ninety degree angle relative to the axis 21 and comprises a same height for each of the plurality of steps 26. As used here, the height is the vertical distance between the stepping surfaces 26b of two adjacent steps 26. Optionally, the stepping surface 26b has a different height for each of the steps 26, the height increasing with each of the steps 26 in a direction away from the longitudinal end 21a.

Figure 3B:
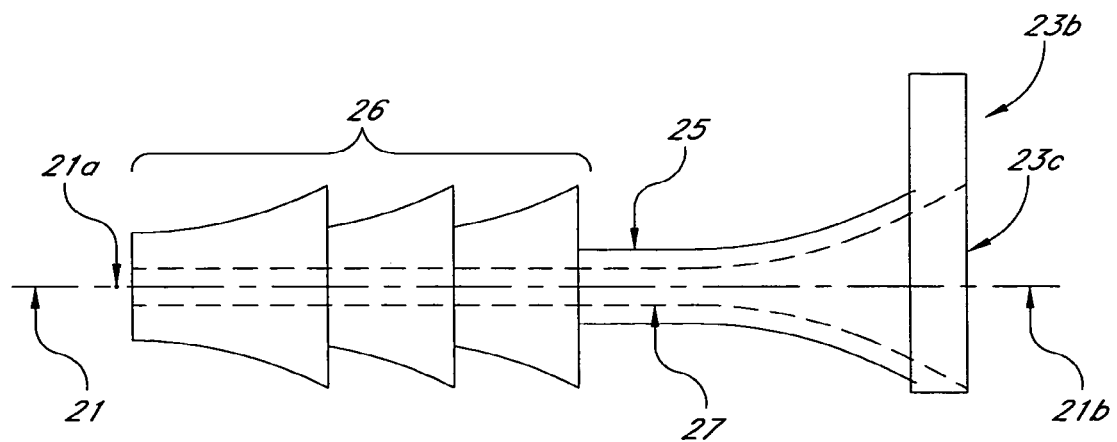
FIG. 3b is a cross-sectional view of a draining attachment having a flared channel.

A channel 27, illustrated by the short dashed lines in FIG. 3, is defined inside the grommet 20 about the axis 21 and extends from an endpoint of the stem at the longitudinal end 21a through the sealing part 22, to the drain aperture 23c at the longitudinal end 21b. As illustrated in FIG. 3b, the channel 27 is optionally flared in the direction of the longitudinal end 21b such that the diameter of the channel 27 at the longitudinal end 21b and the diameter of the drain aperture 23c is greater than the diameter of the channel 27 at the longitudinal end 21a. This feature advantageously provides a larger drain area.

Figure 4:
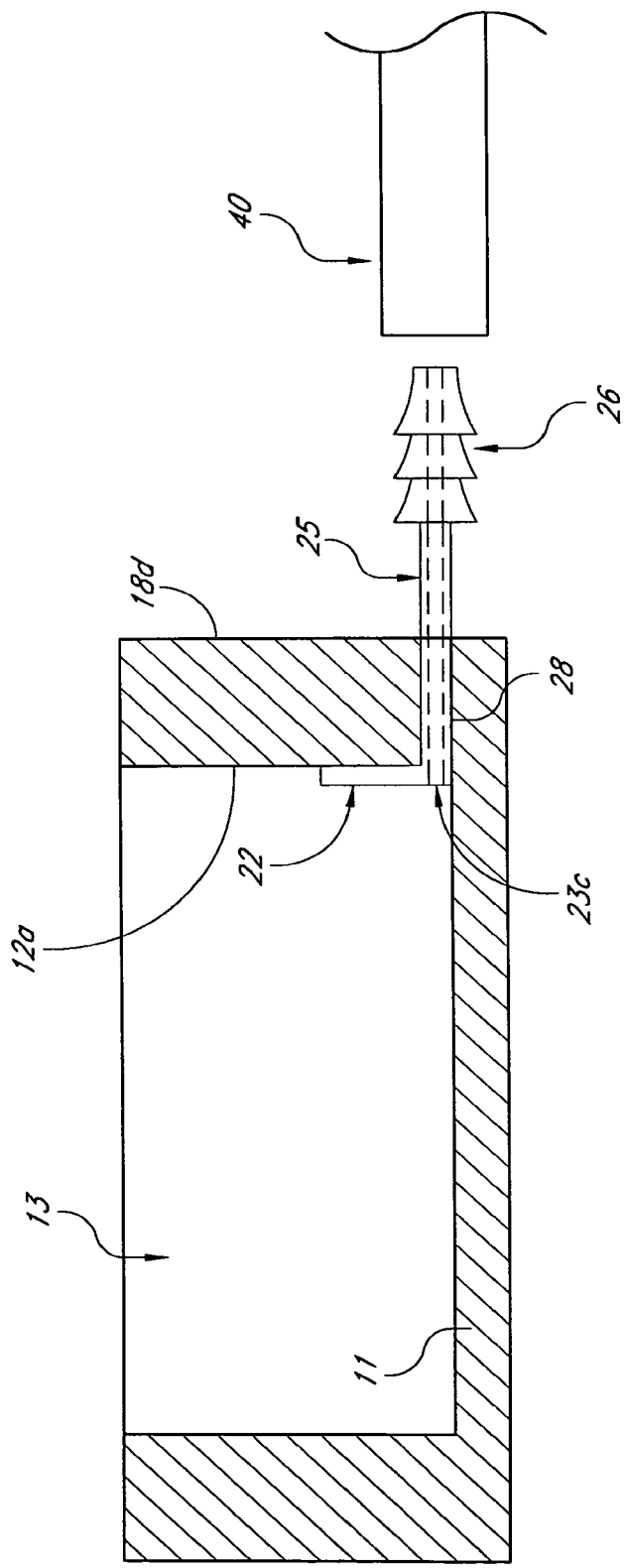
FIG. 4 is a cross-sectional view of the irrigation basin in FIG. 2 incorporating the draining attachment of FIG. 3 to form a drain.

With reference to FIG. 4, use of the grommet 20 to provide a basin of the kit 1 with a drain for use in an active draining process is illustrated therein. In the illustrated embodiment, the grommet 20 is used to provide the basin 10 with a drain.

To form the drain on the basin 10, medical personnel first modify the convertible portion 19 to form a drain. In the illustrated embodiment, the convertible portion 19 is a frangible portion 19 in the form of an annularly extending score 19. However, as discussed above, the convertible portion 19 can comprise a variety of different structures and combination of structures. In the illustrated embodiment, personnel preferably remove the material by punching the material through the wall 12, creating an aperture 28 through the wall 12, extending from the side surface 18d to the inner surface 12a. Medical personnel can use any number of instruments to remove this material. For example, personnel can use their finger, or another instrument with an end surface corresponding to the surface of the material bound by the score 19.

Upon modification of the convertible portion 19, personnel insert the fitting part 24 of the grommet 20 through the aperture 28 at the inner surface 12a so that the sealing surface 23a contacts the inner surface 12a to form a substantially watertight seal. The bottom surface 23d optionally contacts the base 11. Personnel subsequently direct a tube 40 connected to a suction device (not shown) over the longitudinal end 21a of the stem 25, so that the plurality of steps 26 substantially grip the tube 40. Medical personnel can then operate the suction device during the irrigation procedure to draw irrigation fluid from the cavity 13 of the basin 10, through the channel 27 and into the tube 40.

Figure 5:
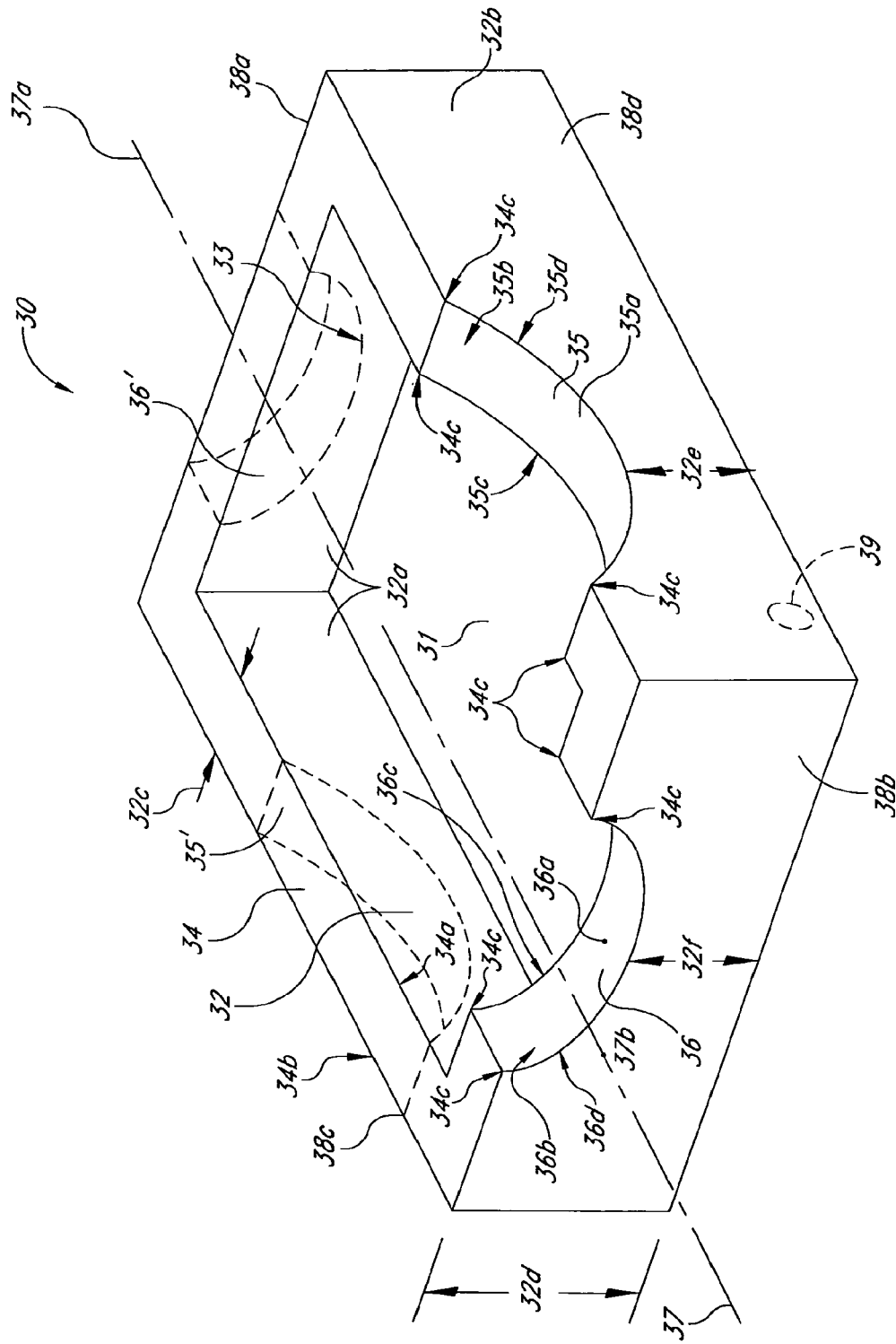
FIG. 5 is a perspective view of another irrigation basin for irrigating a wound on a human extremity.

With reference to FIG. 5, the irrigation basin 30 for irrigating a wound on a human extremity is illustrated therein. For example, the basin 30 can be used for irrigating a wound on a human elbow. The basin 30 comprises a base 31 having a generally rectangular shape and a peripheral wall 32. The basin 30 can have other shapes, such as, but without limitation, round, oval, kidney, and square. The wall 32 is substantially at ninety degrees relative to the resting surface. The base 31 and the wall 32 define a cavity 33 in the center of the basin 30. The peripheral wall 32 also defines an inner surface 32a facing toward the cavity 33 of the basin 30 and an outer surface 32b facing away from the cavity 33 of the basin 30. The basin 30 also comprises an upper periphery 34 having an inner edge 34a and an outer edge 34b. The outer edge 34b preferably joins the upper periphery 34 to the outer surface 32b. In the illustrated embodiment, the periphery 34 defines an inwardly extending flange having a width 32c, supported only by the connection between the outer edge 34b to the wall 32. Alternatively, the thickness of the wall 32 can be sufficient to form the periphery 34. In another option, the inner edge 34a joins the upper periphery 34 to the outer surface 32b and the periphery 34 is supported only by the connection between the inner edge 34a to the wall 32.

The basin 30 is preferably made of a hard plastic material. For example, but without limitation, the basin 30 can be made of polyurethane or polypropylene, among other materials. The material is preferably biocompatible and hypo-allergenic. The basin 30 can also be made of metal, such as, but without limitation, stainless steel. Additionally, the basin 30 is preferably sterilized for use in medical procedures. The basin 30 can optionally be re-useable.

The outer surface 32b comprises two end surfaces 38a, 38b arranged at longitudinal ends 37a, 37b of a major axis 37, respectively, and generally perpendicular to the major axis 37. The outer surface 32b also comprises two side surfaces 38c, 38d extending between the longitudinal ends 37a, 37b and generally parallel to the major axis 37. As used herein, the term "major axis" generally refers to an axis that passes through the basin 30 along the longitudinal direction of the basin 30, i.e., along the greatest dimension or "length" of the basin 30.

The basin 30 further comprises a first recess 35 configured to receive, for example, a human upper arm and a second recess 36 configured to receive, for example, a human forearm. The first recess 35 is disposed along the upper periphery 34 at a side of the basin 30 parallel to the axis 37. The recess 35 bisects the side surface 38d and the inner surface 32a at the side parallel to the axis 37.

The second recess 36 is disposed along the upper periphery 34 at the longitudinal end 37b of the basin 30. The recess 36 bisects the end surface 38b and the inner surface 32a at the longitudinal end 37b. Further, the recesses 35, 36 join to the upper periphery 34 at a plurality of edges 34c.

The basin 30 also optionally includes at least one convertible portion 39 disposed on the outer surface 32b of the wall 32 near the bottom edge of the basin 30, where the bottom edge is the edge that contacts the resting surface. One convertible portion 39 is shows in the illustrated embodiment. The convertible portion 39 can optionally be disposed on the base 31. In one example, the convertible portion 39 can be centrally disposed on the bottom of the base 31. In the illustrated embodiment, the convertible portion 39 is disposed on the side surface 38d.

In the illustrated embodiment, the base 31 of the basin 30 is generally horizontal relative to the resting surface and rectangular in shape. Moreover, the base 31 is substantially at zero degrees relative to the resting surface. However, the base 31 of the basin 30 is not limited to the rectangular shape or to being parallel to the resting surface. For example, the base 31 may be inclined at an angle greater than zero degrees and configured to direct irrigation fluid on the base 31 in the direction of the end surface 38b nearest to the convertible portion 39. For example, the wall 32 can include downwardly protruding portions (not shown) which raise the end 37a relative to the end 37b. Alternatively, the base 31 can be mounted to the wall 32 such that the end of the base 31 adjacent end 37a is higher than the end of the base 31 adjacent the end 37b. In another example, the base 31 can be configured to be adjustably inclined to a plurality of angles such that the end of the base 31 adjacent end 37a is higher than the end of the base 11 adjacent end 37b.

The peripheral wall 32 defines a thickness, which preferably is uniform along the periphery of the wall 32. The thickness is configured to provide the wall 32 with adequate structural rigidity to prevent excessive flexing of the wall 32. Accordingly, the thickness can optionally have various sizes, each of which is capable of providing the wall 32 with adequate structural rigidity. For example, the thickness can be between 1 mm and 5 cm.

The wall 32 also defines a maximum height 32d along the periphery of the wall 32. The maximum height 32d is defined as the distance from the resting surface to the upper periphery 34 of the wall 32. The wall 32 also defines a minimum height 32e at the side of the basin 30 parallel to the axis 37. The minimum height 32e is defined as the distance from the resting surface to a minimum point 35a of the first recess 35. Further, the wall defines a minimum height 32f at the longitudinal end 37b of the basin 30. The minimum height 32f is defined as the distance from the resting surface to a minimum point 36a of the second recess 36. The heights 32d, 32e, 32f are configured to be sufficiently large to allow the cavity 33 defined by the wall 32 and the base 31 to hold a substantial volume of fluid.

The upper periphery 34 in the illustrated embodiment is generally parallel to the axis 37. However, the upper periphery 34 can optionally be inclined inwardly so as to drain liquid falling on the periphery 34 back into the cavity 33. Additionally, the periphery 34 can have a curved surface so that the periphery 34 does not have the edges 34a, 34b and to provide a seamless junction between the upper periphery 34 and the outer surface 32b.

The first recess 35, as illustrated in FIG. 5, extends from the edges 34c of the upper periphery 34 to the minimum point 35a. Moreover, the recess 35 has a curved shape. However, the first recess 35 may optionally have any contoured shape configured to receive, for example, a human upper arm. Accordingly, the recess 15 is not limited to the arcuate shape illustrated in FIG. 5. The recess 35 further comprises a recess surface 35b and edges 35c, 35d. The recess 35 preferably joins to the wall 32 at the edge 35d. Optionally, the recess 35 can join to the wall 32 at the edge 35c. In the illustrated embodiment, the recess surface 35b extends horizontally from the edge 35c to the edge 35d adjacent the side surface 38d. The recess surface 35b can optionally be curved between the inner surface 32a and the side surface 38d to provide a seamless junction between the surface 35b and the surfaces 32a, 38d without the edges 35c, 35d. The recess surface 35b can also optionally be inclined inwardly so as to drain liquid falling on the surface 35b back into the cavity 33. The first recess 35 can also have a contoured juncture with the upper periphery 34 to provide a seamless junction between the recess surface 35b and the upper periphery 34, without the edges 34c.

Similarly, the second recess 36 has a generally curved shape, as illustrated in FIG. 5, and extends from the edges 34c of the upper periphery 34 to the minimum point 36a. However, the second recess 36 may optionally have any contoured shape configured to receive, for example, a human forearm. Accordingly, the recess 36 is not limited to the arcuate shape illustrated in FIG. 5. The recess 36 further comprises a recess surface 36b and edges 36c, 36d. The recess 36 preferably joins to the wall 32 at the edge 36d. Optionally, the recess 36 can join to the wall 32 at the edge 36c. The recess surface 36b extends horizontally from the edge 36c to the edge 36d adjacent the end surface 38b. The recess surface 36b can optionally be curved between the inner surface 32a and the end surface 38b to provide a seamless junction between the surface 36b and the surfaces 32a, 38b without the edges 36c, 36d. The recess surface 36b can also optionally be inclined inwardly so as to drain liquid falling on the surface 36b back into the cavity 33. The second recess 26 can also have a contoured juncture with the upper periphery 34 to provide a seamless junction between the recess surface 36b and the upper periphery 34, without the edges 34c.

As described above with respect to the basin 10, the convertible portion 39 can similarly comprise a variety of structures and combination of structures. Moreover, a plurality of convertible portions 39 can optionally be disposed along the periphery of the wall 32 and the base 31. For example, but without limitation, the convertible portion 39 can comprise a hole 39 formed on the wall 32 covered with a removable cover, such as, but not limited to, a peel-off seal. The cover can be attached to the side wall 38d, for example, with an adhesive.

In another example, the convertible portion 39 can comprise a threaded hole 39 formed on the wall 32 with a threaded plug that covers the hole 39. In still another example, a removable cork can be used to cover the hole 39.

In yet another example, the convertible portion 39 can comprise a nipple 39 having a removable cap, the nipple 39 extending outward from the side wall 38d. The nipple 39 can be molded onto the side wall 38d. Optionally, the nipple 39 can be removably screwed onto the side wall 38d. In another example, the convertible portion 39 can comprise a nipple 39 having a strainer and a removable cover, such as, but not limited to a peel-off seal.

In still another example, the convertible portion 39 can comprise a clamp 39 configured to receive a suction hose, such as a conventional suction hose found in a medical facility, where the clamp 39 is integrally molded or removably attached to the inner surface 32a of the basin 30. In another example, the convertible portion 39 can comprise a removable holder comprising at least one clip disposed over the wall 32 of the basin 30. In still another example, the convertible portion 39 can comprise an aperture on the upper periphery 34 configured to receive a cannula.

According to the illustrated embodiment of the basin 30, the convertible portion 39 is in the form of an annularly extending score 39 defining a frangible portion disposed on the side surface 38d. However, the score 39 can be disposed on any portion of the wall 32 or the base 31. Additionally, a plurality of scores 39 can optionally be disposed on the basin 30. The score 39 is configured to form an aperture through the wall 32 or base 11 to drain the cavity 33 following the removal of the material bounded by the score 39 from the wall 32. The score 39 is preferably disposed near the bottom of the surface 38d, close to the resting surface. However, the score 39 can be disposed in any location capable of providing an effective drain for the cavity 33 upon the removal of the material bounded by the score 39 from the wall 32. Additionally, though the score 39 preferably comprises a circular shape, as shown in the illustrated embodiment, the score 39 can comprise any shape that provides an effective drain for the cavity 33. For example, the score 39 can comprise a slit.

In preparation for the irrigation of an elbow wound, medical personnel remove the cover 2 from the kit 1 and remove the basin 30 from the kit. If the wound is in the elbow area, medical personnel have the patient place the patient's upper arm on the first recess 35 and the patient's forearm on the second recess 36 so that the wound is disposed over the cavity 33 of the basin and faces away from the base 31 of the basin 30.

If medical personnel wish to actively drain the basin 30 during the irrigation procedure, as described above with respect to the basin 10, the personnel modify the convertible portion 39 to create a drain in the basin 30. The basin 30 is then ready to be actively drained. In the illustrated embodiment, where the convertible portion 39 comprises a frangible portion 39, medical personnel can break the frangible portion 39 to create a drain for the basin 30. Personnel can optionally insert a draining device, such as the grommet 20, into the drain and attach a suction hose to the draining device. Personnel can then attach a second end of the suction hose (not shown) to a suction device (not shown) to actively drain the basin 30. As noted above, the basin 30 can comprise a plurality of convertible portions 39 disposed along the periphery of the basin 30, allowing personnel to choose the convertible portion 39 that best accommodates the draining of the basin 30 or create additional drains. The grommet 20 and active draining process are described above.

Medical personnel can also actively drain the basin 30 by attaching the adhesive surface 5a of the cannula 5 to the inner surface 32a of the basin 30 such that an end of the cannula 5 is proximal to the base 31. In another option, the cannula 5 is configured to self-support against the inner surface 32a of the basin 30 without an adhesive surface. Personnel can then attach a second end of the cannula 5 to a suction device, as described above.

Irrigation fluid is then directed to the wound region to remove any contaminants from the wound region. The irrigation fluid directed to the wound region subsequently collects in the cavity 33 of the basin 30. The recesses 35, 36 further improve the fluid-collection ability of the cavity 33 by reducing escape of irrigation fluid through the juncture of the patient's arm with the recesses 35, 36.

The basin 30, as described above, can optionally be configured for irrigating wounds on a human ankle. The first recess 35 can be configured to receive, for example, a human shin, and the second recess 36 can be configured to receive, for example, a human foot. Additionally, the maximum height 32d is greater for the basin 30 configured for irrigation of an ankle wound than for irrigation of an elbow wound.

To irrigate an ankle wound along the outer side of the leg, medical personnel first have the patient sit on the examination table with his or her leg extended. Medical personnel then place the basin 30 under the extended leg of the patient so that the inner side of the patient's leg along the shin region rests on the first recess 35 of the basin 30 and the inner side of the patient's foot rests on the second recess 36 of the basin 30. As used here, the outer side means the side facing away from the patient's body and the inner side means the side facing toward the patient's other leg when the patient stands-up straight. Accordingly, the patient's wound is disposed over the cavity 33 of the basin 30. Likewise, if the wound is in the ankle area along the inner side of the leg, personnel have the patient sit on the examination table with their leg extended. Personnel then place the basin 30 under the extended leg of the patient so that the outer side of the patient's leg along the shin region rests on the first recess 35 of the basin 30 and the outer side of the patient's foot rests on the second recess 36 of the basin 30.

In another embodiment, the basin 30, as described above, can optionally comprise a third recess 36' disposed along the upper periphery 34 opposite the second recess 36, as illustrated by the dashed lines in FIG. 5. The third recess 36' has the same general structure as the second recess 36 and would be identified with similar reference numerals (not shown).

The second and third recess 36, 36' can optionally be configured to receive an upper leg portion of a human anatomy, such as a thigh, and a lower leg portion, such as a calf, respectively. The first recess 35 can be configured to receive, for example, an upper arm portion. Accordingly, the basin 30 can be used for irrigating wounds on the knee area and the elbow area of the human anatomy. Optionally, the first recess 35 can be configured to receive a human foot, so that the basin 30 can be used for irrigating wounds on the knee area and the ankle area of the human anatomy.

In another embodiment, the basin 30 can optionally comprise a fourth recess 35', disposed along the periphery 34 opposite the first recess 35. The fourth recess 35' has the same general structure as the first recess 35 and would be identified with similar reference numerals (not shown). The recesses 35, 36 35', 36' can optionally be sized to have the same dimensions. The recesses 35, 36, 35', 36' can also optionally be sized such that only two of the recesses 35, 36, 35', 36' share the same dimensions. In another example, the recesses 35, 36, 35', 36' can be sized such that only three of the four recesses 35, 36, 35', 36' share the same dimensions. In still another example, the recesses 35, 36, 35', 36' can each have different dimensions. As used herein, the dimension of a recess includes the breadth and depth of the recess. For example, the depth of the first recess is the difference between the maximum height 32d and the minimum height 32e of the first recess 35.

Figure 6:
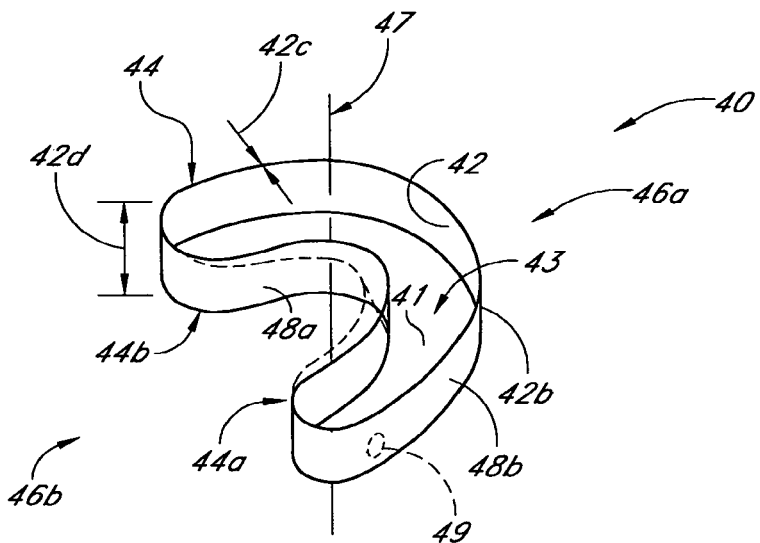
FIG. 6 is a perspective view of another irrigation basin for irrigating a wound on a human extremity.
Figure 6A:
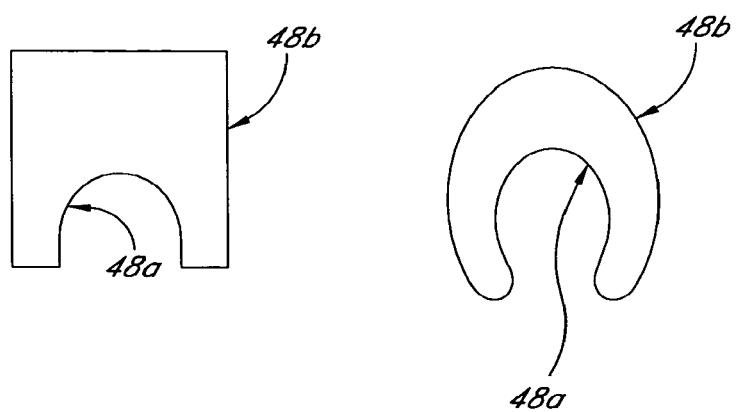
FIG. 6a is a top plan view of an irrigation basin for irrigating a wound on a human extremity having different shapes.
Figure 7:
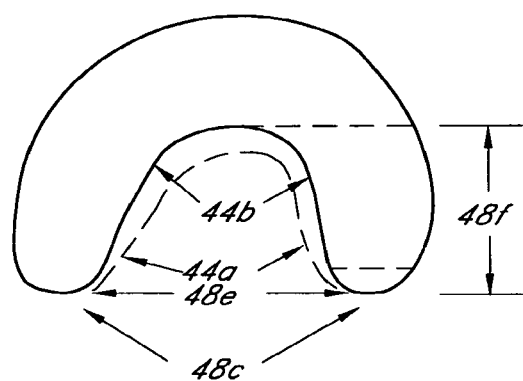
FIG. 7 is a top plan view of the irrigation basin in FIG. 6.

With reference to FIGS. 6 and 7, an irrigation basin 40 for irrigating a wound on a human extremity is illustrated therein. For example, the basin 40 can be used for irrigating a wound on a human shoulder. The basin 40 preferably comprises a base 41 having a generally C-shape and a peripheral wall 42. However, the base 41 can have a variety of other shapes, as illustrated in FIG. 6a. The wall 42 is substantially at ninety degrees relative to the resting surface. The basin 40 preferably also comprises a C-shape. However, the basin 40 can optionally comprise other shapes, such as round, oval, kidney, square and horseshoe. The base 41 and the wall 42 define a cavity 43 in the basin 40. The peripheral wall 42 also defines an inner surface 42a facing toward the cavity 43 of the basin 40 and an outer surface 42b facing away from the cavity 43 of the basin 40. The basin 40 also comprises an upper edge 44. The basin 40 further comprises longitudinal ends 46a, 46b.

The basin 40 is preferably made of a hard plastic material. For example, but without limitation, the basin 40 can be made of polyurethane or polypropylene, among other materials. The material is preferably biocompatible and hypo-allergenic. The basin 40 can also be made of metal, such as, but without limitation, stainless steel. Additionally, the basin 40 is preferably sterilized for use in medical procedures. The basin 40 can optionally be re-useable.

The outer surface 42b comprises a contact region 48a and a surrounding region 48b, wherein both regions 48a, 48b extend around an axis 47. The outer surface 42b further comprises two end regions 48c, each of the end regions disposed on either side of the axis 47. In the illustrated embodiment, the end regions 48c extend on either side of the axis 47 so that the basin 40 has a C-shape. However, the end regions 48c can optionally extend further on either side of the axis 47 so that the basin 40 has a horseshoe shape, as illustrated in FIG. 6a.

Figure 6B:
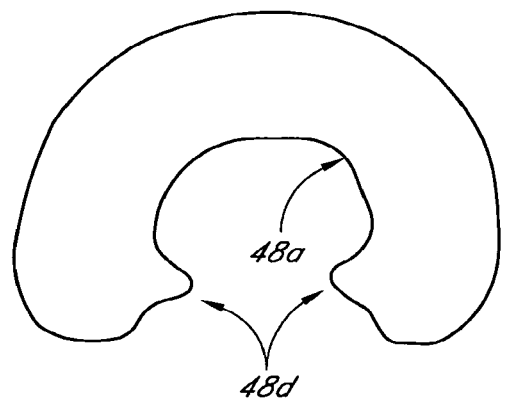
FIG. 6b is a top plan view of an irrigation basin for irrigating a wound on a human extremity having protrusions along the contact region.

The contact region 48a is preferably contoured to receive, for example, a human upper arm region near the shoulder. The contact region 48a optionally comprises a plurality of protrusions 48d extending outwardly from the contact region 48a toward the axis 47, as illustrated in FIG. 6b. As illustrated in FIGS. 6 and 7, the contact region 48a preferably has an arcuate shape defining a breadth 48e and a depth 48f. The breadth 48e is preferably six inches, and more preferably eight inches. The depth 48f is preferably eight inches.

The contact region 48a is not limited to the arcuate shape, but can have any shape capable of receiving, for example, the upper arm. Additionally, an upper edge 44a of the contact region 48a can optionally be inclined toward the axis 47 such that the upper edge 44a of the contact region 48a is closer to the axis 47 than a lower edge 44b of the contact region 48a, as illustrated by the dashed lines in FIGS. 6 and 7. The illustrated embodiment further shows the end regions 48c as having a curved shape. However, the end regions 48c can have any number of shapes, such as, but without limitation, a generally flat shape, as illustrated by the dashed line in FIG. 7.

The basin 40 also optionally includes at least one convertible portion 49 disposed on the outer surface 42b of the wall 42 near the bottom edge of the basin 40, where the bottom edge is the edge that contacts the resting surface. One convertible portion 49 is shown in the illustrated embodiment. The convertible portion 49 can optionally be disposed on the base 41. In one example, the convertible portion 49 can be centrally disposed on the bottom of the base 41. In the illustrated embodiment, the convertible portion 49 is disposed on the surrounding region 48b.

In the illustrated embodiment, the base 41 of the basin 40 is generally horizontal relative to the resting surface and extends around the axis 47. Moreover, the base 41 is substantially at zero degrees relative to the resting surface. However, the base 41 is not limited to being parallel to the resting surface. For example, the base 41 may be inclined at an angle greater than zero degrees and configured to direct irrigation fluid on the base 41 in the direction of the surrounding region 48b nearest to the convertible portion 49. Alternatively, the base 41 can be mounted to the wall 42 such that the end of the base 41 adjacent longitudinal end 46a is higher than the end of the base 41 adjacent the end 46b. In another example, the base 41 can be configured to be adjustably inclined to a plurality of angles such that the end of the base 41 adjacent longitudinal end 46a is higher than the end of the base 41 adjacent the end 46b.

The peripheral wall 42 defines a thickness 42c, which preferably is uniform along the periphery of the wall 42. The thickness 42c is configured to provide the wall 42 with adequate structural rigidity to prevent excessive flexing of the wall 42. Accordingly, the thickness 42c can optionally have various sizes, each of which is capable of providing the wall 42 with adequate structural rigidity. For example, the thickness 42c can be between 1 mm and 5 cm.

The wall 42 also defines a maximum height 42d along the periphery of the wall 42. The maximum height 42d is defined as the distance from the resting surface to the upper edge 44 of the wall 42. The height 42d is configured to be sufficiently large to allow the cavity 43 to hold a substantial volume of fluid.

As described above with respect to the basin 10, the convertible portion 49 can similarly comprise a variety of structures and combination of structures. Moreover, a plurality of convertible portions 49 can optionally be disposed along the periphery of the wall 42 and the base 41. For example, but without limitation, the convertible portion 49 can comprise a hole 49 formed on the wall 42 covered with a removable cover, such as, but not limited to, a peel-off seal. The cover can be attached to the outer surface 42b, for example, with an adhesive.

In another example, the convertible portion 49 can comprises a threaded hole 49 formed on the wall 42 with a threaded plug that covers the hole 49. In still another example, a removable cork can be used to cover the hole 49.

In yet another example, the convertible portion 49 can comprise a nipple 49 having a removable cap, the nipple 49 extending outward from the outer surface 42b. The nipple 49 can be molded onto the outer surface 42b. Optionally, the nipple 49 can be removably screwed onto the outer surface 42b. In another example, the convertible portion 49 can comprise a nipple 49 having a strainer and a removable cover, such as, but not limited to a peel-off seal.

In still another example, the convertible portion 49 can comprise a clamp 49 configured to receive a suction hose, such as a conventional suction hose found in a medical facility, where the clamp 49 is integrally molded or removably attached to the inner surface 42a of the basin 40. In another example, the convertible portion 49 can comprise a removable holder having at least one clip disposed over the wall 42 of the basin 40.

According to the illustrated embodiment of the basin 40, the convertible portion 49 is preferably in the form of an annularly extending score 49 defining a frangible portion disposed on the surrounding region 48b. However, the score 49 can be disposed on any portion of the wall 42 or the base 41. Additionally, a plurality of scores 49 can optionally be disposed on the basin 40. The score 49 is configured to form an aperture through the wall 42 or base 41 to drain the cavity 43 following the removal of the material bounded by the score 49 from the wall 42. The score 49 is preferably disposed near the bottom of the surrounding region 48b, close to the resting surface. However, the score 49 can be disposed in any location capable of providing an effective drain for the cavity 43 upon the removal of the material bounded by the score 49 from the wall 42. Additionally, though the score 49 preferably comprises a circular shape, as shown in the illustrated embodiment, the score 49 can comprise any shape that provides an effective drain for the cavity 43. For example, the score 49 can comprise a slit.

In preparation for the irrigation of a shoulder wound, medical personnel place the basin 40 around the patient's upper arm region so that the contact region 48a comes in contact with the patient's upper arm and so the cavity 43 faces toward the location of the wound on the patient's shoulder region. Personnel preferably place the basin 40 on the patient's upper arm so that the contact region 48a is in contact with the upper arm surface nearest to the wound and the end regions 48c face in a direction away from the wound.

If medical personnel wish to actively drain the basin 40 during the irrigation procedure, the personnel modify the convertible portion 49, as described above with respect to the basin 10, to create a drain in the basin 40. The basin 40 is then ready to be actively drained. In the illustrated embodiment, where the convertible portion 49 comprises a frangible portion 49, personnel can break the frangible portion 49 to create a drain for the basin 40. Personnel can optionally insert a draining device, such as the grommet 20, into the drain and attach a suction hose (not shown) to the draining device. Personnel can then attach a second end of the suction hose to a suction device (not shown) to actively drain the basin 40. As noted above, the basin 40 can comprise a plurality of convertible portions 49 disposed along the periphery of the basin 40, allowing personnel to choose the convertible portion 49 that best accommodates the draining of the basin 40 or create additional drains.

Medical personnel can also actively drain the basin 40 by attaching the adhesive surface 5a of the cannula 5 to the inner surface 42a of the basin 40 such that an end of the cannula 5 is proximal to the base 41. Optionally, the cannula 5 is configured to self-support against the inner surface 42a of the basin 40 without an adhesive surface. Personnel can then attach a second end of the cannula 5 to a suction device, as described above.

Irrigation fluid is then directed to the wound region to remove any contaminants from the wound region. The irrigation fluid directed to the wound region subsequently collects in the cavity 43 of the basin 40.

The basin 40, as described above, can optionally be configured for the irrigation of wounds on a variety of human extremities. For example, the contact region 48a can be configured to receive a lower leg region. In another example, the contact region 48a can be configured to receive an upper leg human region. The maximum height 42d of the wall 42 is preferably taller if the basin is configured for irrigation of leg wounds than arm wounds.

In addition, the basin 40 can optionally be configured for the irrigation of wounds on a human knee while the knee is in a flexed position. For example the basin 40 can comprise an upper periphery (not shown) having an inner edge and an outer edge, where the outer edge joins the upper periphery to the wall 42. The periphery can be an inwardly extending flange having a width and supported only by the connection between the outer edge to the wall 42. In another option, the periphery can be supported only by the connection between the inner edge to the wall 42.

The basin 40 can further comprise a recess (not shown) similar to the first recess 15 described above with respect to the basin 10. The recess is preferably disposed along the upper periphery and is configured to receive, for example, a human thigh. The recess bisects the wall 42 preferably at a location opposite the contact region 48a, which is preferably U-shaped and configured to receive a lower leg region, so that the recess and contact region 48a are aligned. The recess also preferably has a generally arcuate shape. However, the recess can have any contoured shape configured to receive a thigh. The lower edge 44b of the contact region 48a can optionally be inclined toward the axis 47 such that the lower edge 44b is closer to the axis 47 than the upper edge 44a of the contact region. The basin 40 can thus be advantageously configured for use in irrigation of a wound on a flexed knee, resulting in a thorough cleaning of a knee wound.

To irrigate a wound on a flexed knee, the user places the basin 40 under the patient's leg, such that the patient's upper leg region, such as a thigh, rests on the recess. The user also has the patient flex the injured knee such that the patient's lower leg region, such as the calf, comes in contact with the contact region 48a. Accordingly, the wound is disposed over the basin 40. Irrigation fluid is then directed to the wound region as previously described.

Figure 7A:
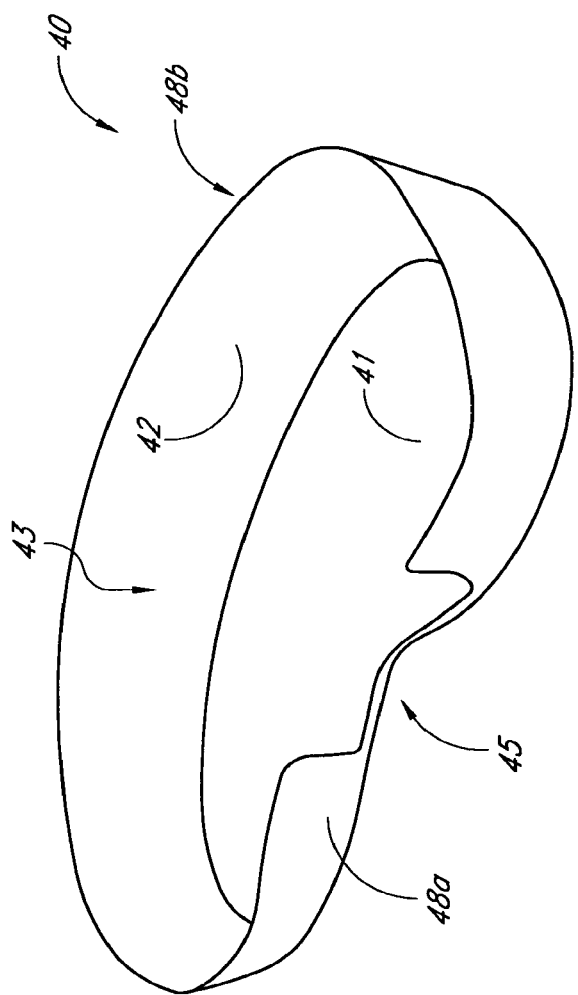
FIG. 7a is a perspective view of another irrigation basin for irrigating a wound on a human extremity.

In another embodiment, the basin 40 can comprise the general shape of a kidney basin, as illustrated in FIG. 7a. The basin 40 has a contact region 48a and a surrounding region 48b. The basin 40 preferably defines an aperture 45 along the contact region for receiving a human extremity to irrigate a wound on the extremity.

To irrigate a wound on a human extremity with the basin 40 illustrated in FIG. 7a, medical personnel place the basin 40 under the patient's extremity so that a region of the extremity rests in the aperture 45 and the wound or fracture is disposed over the cavity 43 of the basin 40. Personnel then direct irrigation fluid to the wound as previously described.

Figure 8:
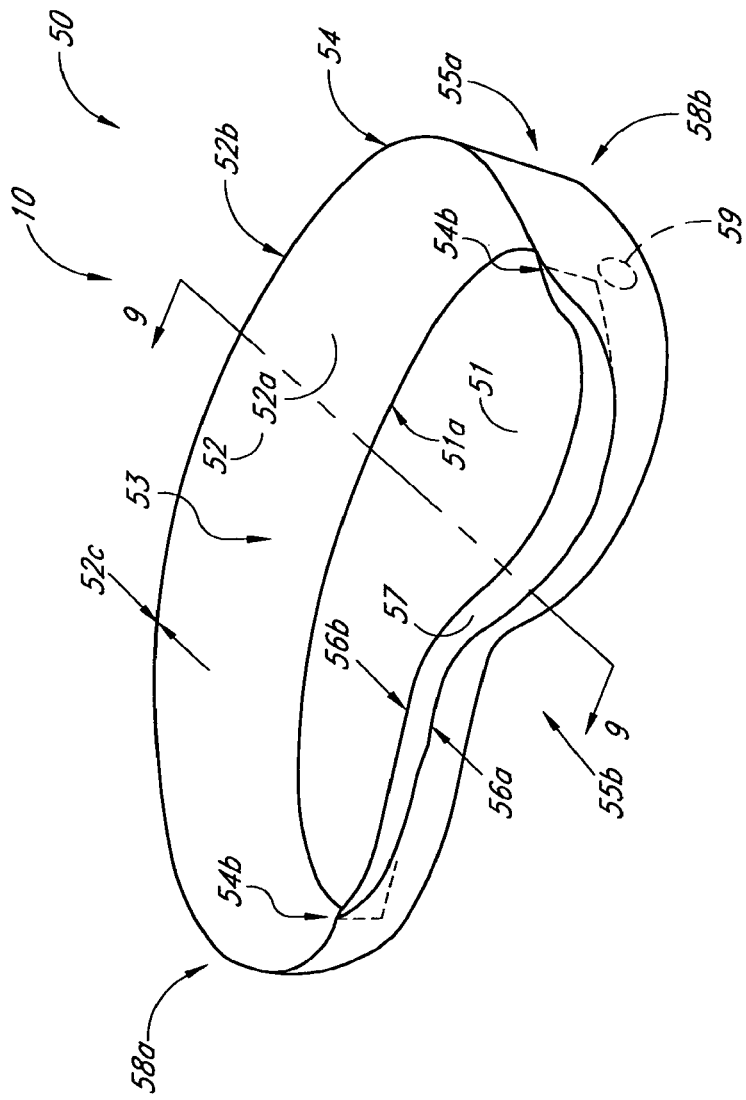
FIG. 8 is a perspective view of another irrigation basin for irrigating a wound on a human extremity.

With reference to FIG. 8, a basin 50 for irrigating a wound on a human extremity is illustrated therein. For example, the basin 50 can be used for irrigating a wound on a human hip. The basin 50 comprises a base 51, preferably having a generally kidney shape, and a peripheral wall 52. The wall 52 is preferably substantially at ninety degrees relative to the resting surface. The base 51 and the wall 52 define a cavity 53 in the basin 50. The peripheral wall 52 also defines an inner surface 52a facing toward the cavity 53 and an outer surface 52b facing away from the cavity 53 of the basin 50. The basin 50 also comprises an upper edge 54 and longitudinal ends 58a, 58b. The basin 50 further comprises a curved region 55a and an arched region 55b disposed opposite the curved region 55a.

The basin 50 is preferably made of a hard plastic material. For example, but without limitation, the basin 50 can be made of polyurethane or polypropylene, among other materials. The material is preferably biocompatible and hypo-allergenic. The basin 50 can also be made of metal, such as, but without limitation, stainless steel. Additionally, the basin 50 is preferably sterilized for use in medical procedures. The basin 50 can optionally be re-useable.

The basin 50 also optionally includes at least one convertible portion 59 disposed on the outer surface 52b of the wall 52 near the bottom edge of the basin 50, where the bottom edge is the edge that contacts the resting surface. One convertible portion 59 is shown in the illustrated embodiment. The convertible portion 59 can optionally be disposed on the base 51. In one example, the convertible portion 59 can be centrally disposed on the bottom of the base 51. In the illustrated embodiment, the convertible portion 59 is disposed on the curved region 55a.

Figure 9:
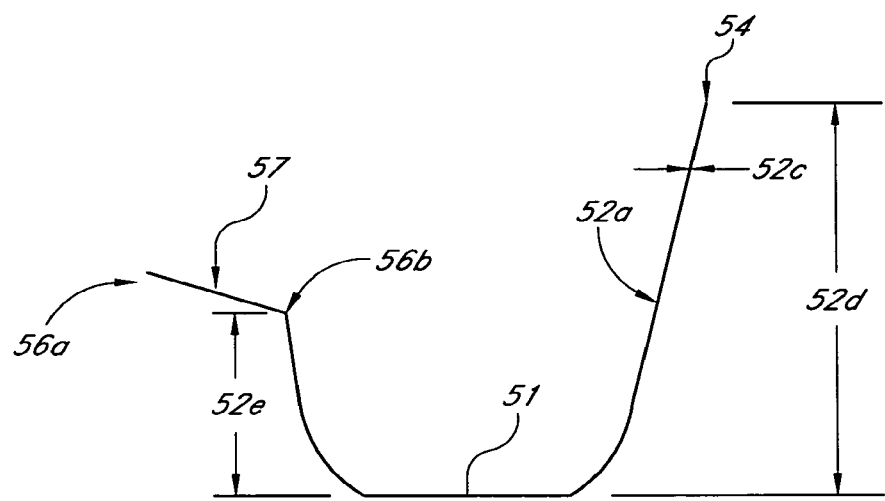
FIG. 9 is a cross-sectional view of the irrigation basin taken along line 9-9 of FIG. 8.

In the illustrated embodiment, the base 51 of the basin 50 is generally horizontal relative to the resting surface and defines an edge 51a at the juncture with the inner surface 52a. Moreover, the base 51 is substantially at zero degrees relative to the resting surface. However, the base 51 is not limited to being parallel to the resting surface. For example, the base 51 may be inclined at an angle greater than zero degrees and configured to direct irrigation fluid on the base 51 in the direction of the curved region 55a nearest to the convertible portion 59. For example, the wall 52 can include downwardly protruding portions (not shown) which raise the end 58a relative to the end 58b. Alternatively, the base 51 can be mounted to the wall 52 such that the end of the base 51 adjacent end 58a is higher than the end of the base 51 adjacent the end 58b. Additionally, the base 51 may join to the inner surface 52a through a contoured juncture so that the base 51 does not define the edge 51a, as illustrated in FIG. 9. In another example, the base 51 can be configured to be adjustably inclined to a plurality of angles such that the end of the base 51 adjacent end 58a is higher than the end of the base 51 adjacent the end 58b.

The peripheral wall 52 defines a thickness 52c, which preferably is uniform along the periphery of the wall 52. The thickness 52c is configured to provide the wall 52 with adequate structural rigidity to prevent excessive flexing of the wall 52. Accordingly, the thickness 52c may optionally have various sizes, each of which is capable of providing the wall 52 with adequate structural rigidity. For example, the thickness can be between 1 mm and 5 cm.

The upper edge 54 of the wall 52 comprises a recessed edge 56a that preferably extends along the arched region 55b of the basin 50 between junctures 54b. The recessed edge 56a is recessed downward relative to the upper edge 54. In the illustrated embodiment, the junctures 54b that connect the upper edge 54 to the recessed edge 56a have a contoured shape. For example, the junctures 54b are curved to provide a continuous transition between the recessed edge 56a and the upper edge 54. However, the junctures can have any number of shapes, such as, but without limitation, a step shape as illustrated by the dashed line in FIG. 8.

The basin 50 further comprises an inner edge 56b formed on the inner surface 52a and disposed between the junctures

Figure 10:
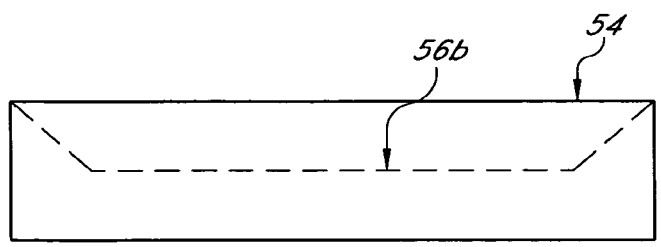
FIG. 10 is a side elevational view of the irrigation basin as viewed along arrow 10 of FIG. 8.

54*b*. The inner edge 56*b* is recessed downward relative to the upper edge 54 as illustrated in FIGS. 9 and 10. The inner edge 56*b* may optionally also be recessed downward relative to the recessed edge 56*a* as illustrated in FIG. 9. In the illustrated embodiment, the junctures 54*b* that connect the upper edge 54 to the inner edge 56*b* have a contoured shape to provide a continuous transition between the inner edge 56*b* and the upper edge 54. However, the junctures 54*b* can have any number of shapes as discussed above.

The recessed edge 56*a* and the inner edge 56*b* define a contact region 57 that extends between the edges 56*a*, 56*b*. In the illustrated embodiment, the contact region 57 is an outwardly extending flange having a width 57*a*, supported only by the connection between the recessed edge 56*a* to the wall 52. In another option, the inner edge 56*b* joins the contact region 57 to the outer surface 52*b* and the contact region 57 is supported only by the connection between the inner edge 56*b* to the wall 52. The contact region 57 is recessed downward relative to the upper edge 54, as shown in FIG. 9, and is configured to receive, for example, a human hip. Moreover, the contact region 57 is preferably configured to receive the human anatomy from a point above the hip to a point below the buttock. The contact region 57 is also preferably horizontal. As used here, horizontal means substantially at zero degrees relative to the resting surface. However, the contact region 57 can optionally be inclined inwardly so as to drain liquid falling on the contact region 57 back into the cavity 53, as shown in FIG. 9.

The wall 52 defines a maximum height 52*d* along the periphery of the wall 52. The maximum height 52*d* is defined as the distance from the resting surface to the upper edge 54 of the wall 52. The wall 52 also defines a minimum height 52*e* defined as the distance from the resting surface to the inner edge 56*b*. The heights 52*d*, 52*e* are configured to be sufficiently large to allow the cavity 53 defined by the wall 52 and the base 51 to hold a substantial volume of fluid.

As described above with respect to the basin 10, the convertible portion 59 can similarly comprise a variety of structures and combination of structures. Moreover, a plurality of convertible portions 59 can optionally be disposed along the periphery of the wall 52 and the base 51. For example, but without limitation, the convertible portion 59 can comprise a hole 59 formed on the wall 52 covered with a removable cover, such as, but not limited to, a peel-off seal. The cover can be attached to the outer surface 52*b*, for example, with an adhesive.

In another example, the convertible portion 59 can comprise a threaded hole 59 formed on the wall 52 with a threaded plug that covers the hole 59. In still another example, a removable cork can be used to cover the hole 59.

In yet another example, the convertible portion 59 can comprise a nipple 59 having a removable cap, the nipple 59 extending outward from the outer surface 52*b*. The nipple 59 can be molded onto the outer surface 52*b*. Optionally, the nipple 59 can be removably screwed onto the outer surface 52*b*. In another example, the convertible portion 59 can comprise a nipple 59 having a strainer and a removable cover, such as, but not limited to a peel-off seal.

In still another example, the convertible portion 59 can comprise a clamp 59 configured to receive a suction hose, such as a conventional suction hose found in a medical facility, where the clamp 59 is integrally molded or removably attached to the inner surface 52*a* of the basin 50. In another example, the convertible portion 59 can comprise a removable holder having at least one clip disposed over the wall 52 of the basin 50.

According to the illustrated embodiment of the basin 50, the convertible portion 59 is preferably in the form of an annularly extending score 59 defining a frangible portion disposed on the curved region 55*a*. However, the score 59 can be disposed on any portion of the wall 52 or the base 51. Additionally, a plurality of scores 59 can optionally be disposed on the basin 50. The score 59 is configured to form an aperture through the wall 52 or base 51 to drain the cavity 53 following the removal of the material bounded by the score 59 from the wall 52. The score 59 is preferably disposed near the bottom of the curved region 55*a*, close to the resting surface. However, the score 59 may be disposed in any location capable of providing an effective drain for the cavity 53 upon the removal of the material bounded by the score 59 from the wall 52. Additionally, though the score 59 preferably comprises a circular shape, as shown in the illustrated embodiment, the score 59 can comprise any shape that provides an effective drain for the cavity 53. For example, the score 59 can comprise a slit.

In preparation for the irrigation of a hip wound, medical personnel have the patient lay on their side on the examination table so that the wound on the hip faces away from the table. Personnel then place the basin 50 adjacent the patient's hip so that the hip rests on the contact region 57 from a point above the hip to a point below the buttock. Accordingly, the contact region 57 receives the injured hip and the wound faces toward the cavity 53. Personnel then direct irrigation fluid with an irrigation device to the wound region to remove any contaminants from the wound region. Because the contact region 57 is recessed relative to the upper edge 54, the upper edge 54 advantageously acts as a shield during the irrigation procedure, effectively directing irrigation fluid toward the cavity 53. The irrigation fluid directed to the wound region subsequently collects in the cavity 53 of the basin 50.

If medical personnel wish to actively drain the basin 50 during the irrigation procedure, personnel modify the convertible portion 59, as described above with respect to the basin 10, to create a drain in the basin 50. The basin 50 is then ready to be actively drained. In the illustrated embodiment, where the convertible portion 59 comprises a frangible portion 59, personnel can break the frangible portion 59 to create a drain for the basin 50. Personnel can optionally insert a draining device, such as the grommet 20, into the drain and attach a suction hose to the draining device. Personnel can then attach a second end of the suction hose to a suction device to actively drain the basin 50. As noted above, the basin 50 can comprise a plurality of convertible portions 59 disposed along the periphery of the basin 50, allowing personnel to choose the convertible portion 59 that best accommodates the draining of the basin 50 or create additional drains.

Medical personnel can also actively drain the basin 50 by attaching the adhesive surface 5*a* of the cannula 5 to the inner surface 52*a* of the basin 50 such that an end of the cannula 5 is proximal to the base 51. Optionally, the cannula 5 is configured to self-support against the inner surface 52*a* of the basin 50 without an adhesive surface. Personnel can then attach a second end of the cannula 5 to a suction device, as described above.

Figure 11:
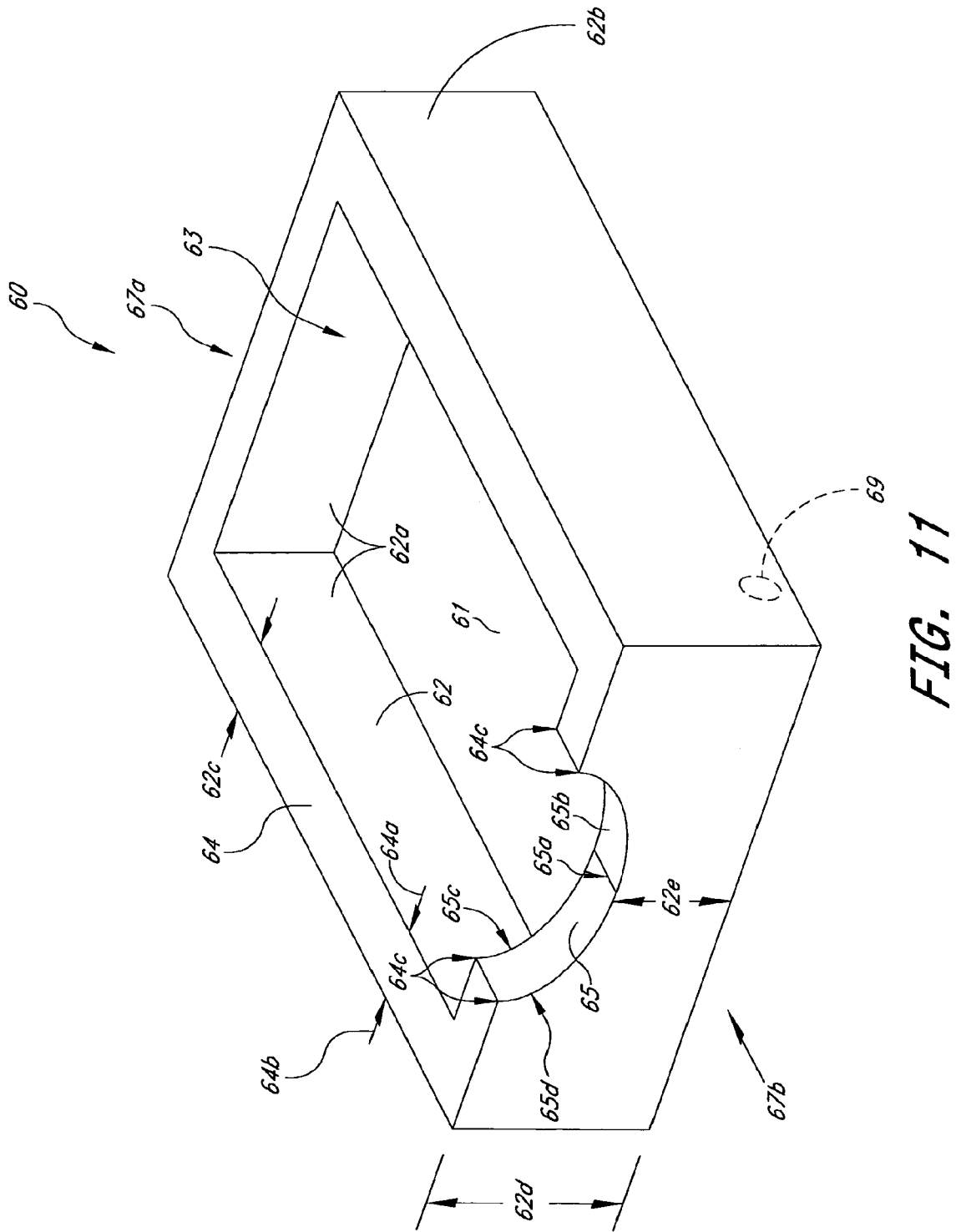
FIG. 11 is a perspective view of another irrigation basin for irrigating a wound on a human extremity.

With reference to FIG. 11, an irrigation basin 60 for irrigating a wound on a human anatomy is illustrated therein. For example, the basin 60 can be used for irrigating a wound on a lower arm region or a lower leg region of the human anatomy. The basin 60 comprises a base 61 having a generally rectangular shape and a peripheral wall 62. The basin 60 can have other shapes, such as, but without limitation, round, oval, kidney, and square. The wall 62 is preferably substantially at ninety degrees relative to a resting surface upon which the basin 60 rests. The base 61 and the wall 62 define a cavity 63 in the center of the basin 60. The peripheral wall 62 also defines an inner surface 62a facing toward the cavity 63 of the basin 60 and an outer surface 62b facing away from the cavity 63 of the basin 60. The basin 60 also comprises an upper periphery 64 having an inner edge 64a and an outer edge 64b. The outer edge 64b joins the upper periphery 64 to the outer surface 62b. In the illustrated embodiment, the periphery 64 defines an inwardly extending flange having a width 62c, supported only by the connection between the outer edge 64b to the wall 62. Alternatively, the thickness of the wall 62 can be sufficient to form the periphery 64. In another option, the inner edge 64a joins the upper periphery 64 to the outer surface 62b and the periphery 64 is supported only by the connection between the inner edge 64a to the wall 62.

The basin 60 is preferably made of a hard plastic material. For example, but without limitation, the basin 60 can be made of polyurethane or polypropylene, among other materials. The material is preferably biocompatible and hypo-allergenic. The basin 60 can also be made of metal, such as, but without limitation, stainless steel. Additionally, the basin 60 is preferably sterilized for use in medical procedures. The basin 60 can optionally be re-useable.

The basin 60 comprises a recess 65 configured to receive a human extremity. For example, the recess 65 can be configured to receive a human forearm to irrigate a wound located below a human elbow. In another example, the recess 65 can be configured to receive a human calf to irrigate a wound located below a human knee. The recess 65 is disposed along the upper periphery 64 at one end of the basin 60 and bisects the outer surface 62b and the inner surface 62a. The recess 15 joins to the upper periphery 14 at edges 14c.

The basin 60 also optionally includes at least one convertible portion 69 disposed on the outer surface 62b of the wall 62 near the bottom edge of the basin 60, where the bottom edge is the edge that contacts the resting surface. One convertible portion 69 is shown in the illustrated embodiment. The convertible portion 69 can optionally be disposed on the base 61. In one example, the convertible portion 69 can be centrally disposed on the bottom of the base 61.

As shown in FIG. 11, the base 61 of the basin 60 is generally horizontal relative to the resting surface and rectangular in shape. Moreover, the base 61 is substantially at zero degrees relative to the resting surface. However, the base 61 of the basin 60 is not limited to the rectangular shape or to being parallel to the resting surface. For example, the base 61 may be inclined at an angle greater than zero degrees and configured to direct irrigation fluid on the base 61 in the direction of the inner surface 62a nearest to the convertible portion 69. For example, the wall 62 can include downwardly protruding portions (not shown) which raise an end 67a relative to an end 67b. Alternatively, the base 61 can be mounted to the wall 62 such that the end of the base 61 adjacent end 67a is higher than the end of the base 61 adjacent end 67b. In another example, the base 61 can be configured to be adjustably inclined to a plurality of angles such that the end of the base 61 adjacent end 67a is higher than the end of the base 61 adjacent the end 67b.

The peripheral wall 62 defines a thickness, which preferably is uniform along the periphery of the wall 62. The thickness is configured to provide the wall 62 with adequate structural rigidity to prevent excessive flexing of the wall 62. Accordingly, the thickness can optionally have various sizes, each of which is capable of providing the wall 62 with adequate structural rigidity. For example, the thickness can be between 1 mm and 5 cm.

The wall 62 defines a maximum height 62d along the periphery of the wall 62. The maximum height 62d is defined as the distance from the resting surface to the upper periphery 64 of the wall 62. The wall 62 also defines a minimum height 62e at the end 67b of the basin. The minimum height 62e is defined as the distance from the resting surface to a minimum point 65a of the recess 65. The heights 62d, 62e are configured to be sufficiently large to allow the cavity 63 to hold a substantial volume of fluid.

The upper periphery 64 in the illustrated embodiment is generally parallel to the resting surface. However, the upper periphery 64 can optionally be inclined inwardly so as to drain liquid falling on the periphery 64 back into the cavity 63. Additionally, the periphery 64 can have a curved surface so that the periphery 64 does not have the edge 64b to provide a seamless junction between the upper periphery 64 and the outer surface 62b.

The recess 65, as illustrated in FIG. 11, extends from the edges 64c of the upper periphery 64 to the minimum point 65a. Moreover, the recess 65 has a curved shape. However, the recess 65 may optionally have any contoured shape configured to receive a human extremity. Accordingly, the recess 65 is not limited to the arcuate shape illustrated in FIG. 11. The recess 65 further comprises a recess surface 65b and edges 65c, 65d. The recess 65 preferably joins to the wall 62 at the edge 65d. Optionally, the recess 65 can join to the wall 62 at the edge 65c. In the illustrated embodiment, the recess surface 65b extends horizontally from the edge 65c to the edge 65d adjacent the outer surface 62b. The recess surface 65b can optionally be curved between the inner surface 62a and the outer surface 62b to provide a seamless junction between the surface 65b and the surfaces 62a, 62b without the edge 65d. The recess surface 65b can also optionally be inclined inwardly so as to drain liquid falling on the surface 65b back into the cavity 63. The recess 65 may also have a contoured juncture with the upper periphery 64 to provide a seamless junction between the recess surface 65b and the upper periphery 64, without the edges 64c.

As described above with respect to the basin 10, the convertible portion 69 can similarly comprise a variety of structures and combination of structures. Moreover, a plurality of convertible portions 69 can optionally be disposed along the periphery of the wall 62 and the base 61. For example, but without limitation, the convertible portion 69 can comprise a hole 69 formed on wall 62 covered with a removable cover, such as, but not limited to, a peel-off seal. The cover can be attached to the outer wall 62b, for example, with an adhesive.

In another example, the convertible portion 69 can comprise a threaded hole 69 formed on the wall 62 with a threaded plug that covers the hole 69. In still another example, a removable cork can be used to cover the hole 69.

In yet another example, the convertible portion 69 can comprise a nipple 69 having a removable cap, the nipple 69 extending outward from the outer wall 62b. The nipple 69 can be molded onto the outer wall 62b. Optionally, the nipple 69 can be removably screwed onto the outer wall 62b. In another example, the convertible portion 69 can comprise a nipple 69 having a strainer and a removable cover, such as, but not limited to a peel-off seal.

In still another example, the convertible portion 69 can comprise a clamp 69 configured to receive a suction hose, such as a conventional suction hose found in a medical facility, where the clamp 69 is integrally molded or removably attached to the inner surface 62a of the basin 60. In another example, the convertible portion 69 can comprise a removable holder having at least one clip disposed over the wall 62 of the basin 60. In another example, the convertible portion can comprise an aperture on the upper periphery 64 configured to receive a cannula.

According to the illustrated embodiment of the basin 60, the convertible portion 69 is in the form of an annularly extending score defining a frangible portion disposed on the outer surface 62b. However, the score 69 may be disposed on any portion of the wall 62 or the base 61. Additionally, a plurality of scores 69 can optionally be disposed on the basin 60. The score 69 is configured to form an aperture through the wall 62 or base 61 to drain the cavity 63 following the removal of the material bounded by the score 69 from the wall 62. The score 69 is preferably disposed near the bottom of the surface 62b, close to the resting surface. However, the score 69 can be disposed in any location capable of providing an effective drain for the cavity 63 upon the removal of the material bounded by the score 69 from the wall 62. Additionally, though the score 69 preferably comprises a circular shape, as shown in the illustrated embodiment, the score 69 can comprise any shape that provides an effective drain for the cavity 63. For example, the score 69 can comprise a slit.

In preparation for the irrigation of a wound on a human extremity, if the wound is located below the patient's elbow, medical personnel place the basin 60 below the patient's arm such that the patient's forearm rests on the recess 65. Alternatively, if the wound is located below the patient's knee, personnel place the basin 60 below the patient's leg such that the patient's calf rests on the recess 65. Accordingly, the patient's wound is disposed over the cavity 63 of the basin 60.

If personnel wish to actively drain the basin 60 during the irrigation procedure, personnel modify the convertible portion 69, as described above with respect to the basin 10, to create a drain in the basin 60. The basin 60 is then ready to be actively drained. In the illustrated embodiment, where the convertible portion 69 comprises a frangible portion 69, personnel can break the frangible portion 69 to create a drain for the basin 60. Personnel can optionally insert a draining device, such as the grommet 20, into the drain and attach a suction hose to the draining device. Personnel can then attach a second end of the suction hose to a suction device to actively drain the basin 60. As noted above, the basin 60 can comprise a plurality of convertible portions 69 disposed along the periphery of the basin 60, allowing personnel to choose the convertible portion 69 that best accommodates the draining of the basin 60 or create additional drains.

Medical personnel can also actively drain the basin 60 by attaching the adhesive surface 5a of the cannula 5 to the inner surface 62a of the basin 60 such that an end of the cannula 5 is proximal to the base 61. Optionally, the cannula 5 is configured to self-support against the inner surface 62a of the basin 60 without an adhesive surface. Personnel can then attach a second end of the cannula 5 to a suction device, as described above.

Irrigation fluid is then directed to the wound region to remove any contaminants from the wound region. The irrigation fluid directed to the wound region subsequently collects in the cavity 63 of the basin 60. The recess 65 advantageously improves the fluid-collection ability of the cavity 63 by reducing escape of irrigation fluid through the juncture of the extremity with the recess 65.

Figure 12:
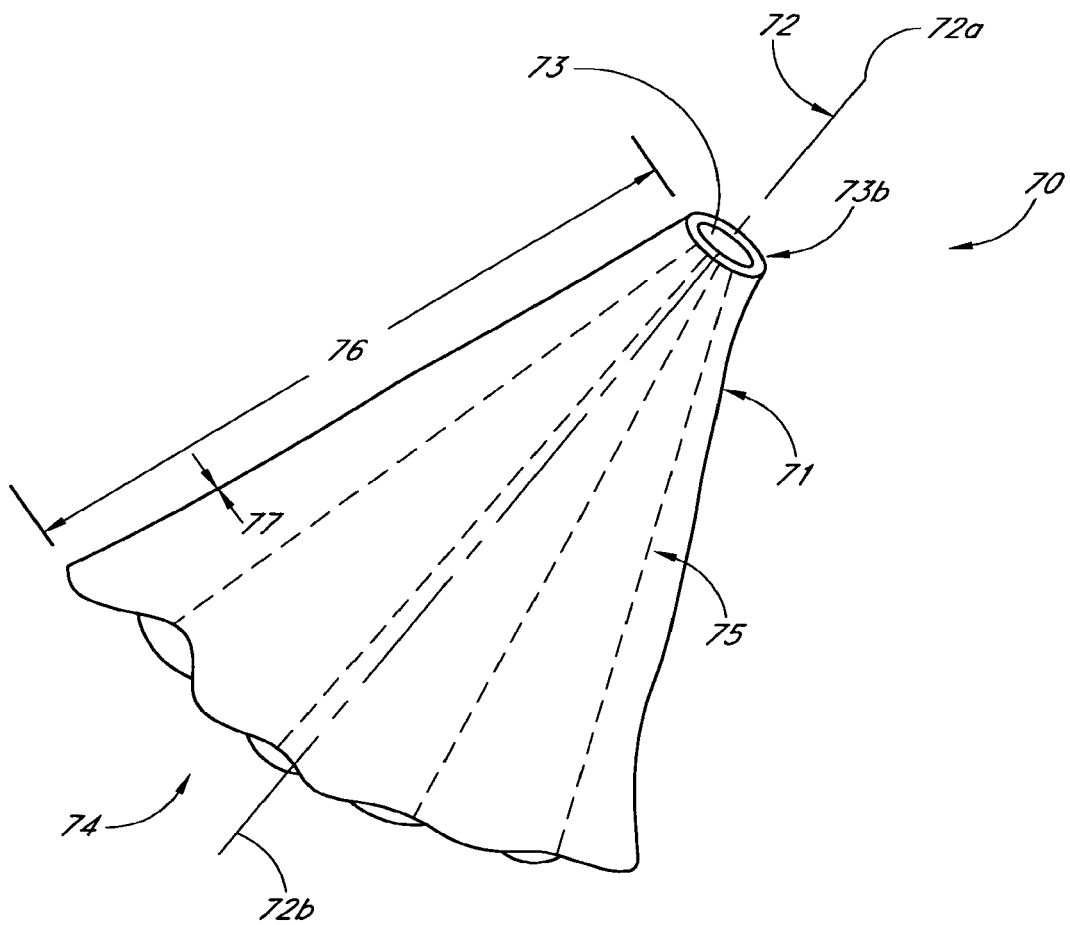
FIG. 12 is a perspective view of an irrigation shield.

With reference to FIG. 12, an irrigation shield 70 is illustrated therein. The irrigation shield 70 comprises a sheet 71 and an aperture 73 disposed at a central portion of the sheet 71. The aperture 73 is configured to be stretched from a resting state to an enlarged state. The sheet 71 is flexible and thus can be shaped to define an open end 74.

An elastic member 73b preferably attaches circumferentially to the sheet 71, around the aperture 73 and is configured to be modified from a resting state to an enlarged state for use with an irrigation device such as the one disclosed in U.S. Pat. No. 6,156,004, discussed below. The member 73b is further configured to generate a gripping force. In the illustrated embodiment, the elastic member 73b is an elastic band. The elastic member 73b can optionally be a latex portion attached circumferentially around the aperture 73, the latex portion having an elastically enlargeable opening configured to receive the irrigation device. The member 73b is preferably attached to the sheet 71 with glue. However, the member 73b can be attached to the sheet 71 in a number of ways, such as, but without limitation, by being sewn to the sheet 71.

The sheet 71 is preferably transparent and made of a flexible material. For example, the sheet 71 can be made of polyurethane or polypropylene. In the illustrated embodiment, the sheet defines an umbrella shape extending along an axis 72 and has a plurality of pleats 75 extending between the aperture 73 at the longitudinal end 72a and the open end 74 at the longitudinal end 72b. However, the sheet 71 can optionally have no pleats 75. Moreover, the sheet 71 is not limited to defining an umbrella shape, but can define one of a variety of shapes. For example, but without limitation, the sheet 71 can define a circular shape, a square shape, a rectangular shape, a star shape, a diamond shape, and a half-circle shape.

The sheet 71 comprises a length 76 defined as the distance between the aperture 73 at the longitudinal end 72a to the open end 74 at the longitudinal end 72b. The length 76 is preferably four feet. The length 76 of the sheet 71 can optionally be shortened, for example with scissors, as desired during an irrigation procedure. The sheet 71 also comprises a thickness 77. The thickness 77 may be any thickness that adequately provides the sheet 71 with the necessary flexibility, and allows the sheet 71 to be folded compactly to fit in the cover 2 of the kit 1. For example, the thickness 77 preferably is from 0.001 inch to 0.02 inch.

Figure 13:
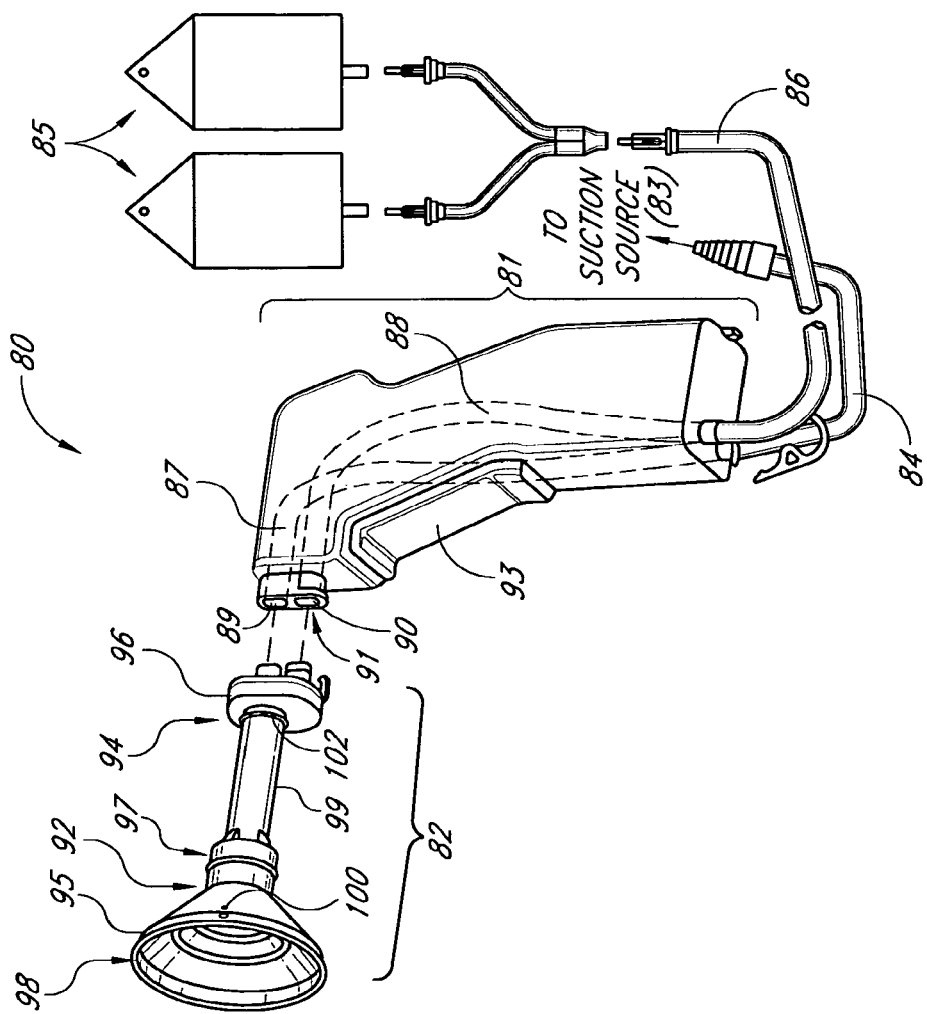
FIG. 13 is a perspective view of a conventional irrigation device.

A typical irrigation device 80 is illustrated in FIG. 13. The device 80 comprises an irrigation handpiece 81, and a suction irrigation tip 82 that is detachably connected to the handpiece 81. The handpiece 81 is connected to a suction source 83 through a flexible suction tubing 84, and to an irrigation source 85 through flexible irrigation tubing 86. A suction lumen 87 and an irrigation lumen 88, both shown in phantom, extend through the entire length of the handpiece 81. The suction lumen 87 connects to the suction source 83 at one end and to a suction port 89 at a second end. The irrigation lumen 88 connects to the irrigation source 85 at one end and to an irrigation port 90 at a second end. Both ports 89, 90 are formed in a fitting 91 at the distal end of the handpiece 81.

When the tip 82 is connected to the handpiece 81 and the handpiece 81 is energized, irrigation fluid passes through the irrigation port 90 and into the tip 82. The irrigation fluid is emitted from a distal end 92 of the tip 82 at a frequency controlled by the handpiece trigger 93. The tip 82 includes a flexible splash shield 95 and connector 96. The connector 96 is disposed at a proximal end 94 of the tip 82 and detachably connects the tip 82 to the handpiece 81. The flexible shield 95 includes a proximal collar 97 and a conical body that diverges in a distal direction to a distal rim 98. The collar 97 is slidably mounted to an irrigation tube 99 comprised by the tip 82. Vent holes 100 disposed on the shield 95 are configured to prevent the shield from collapsing when the irrigation device 80 is operated in a suction mode. A stop ridge 102 may circumscribe the proximal end of the irrigation tube 99 to prevent the splash shield 95 from being retracted into contact with the connector 96.

During operation, medical personnel connect the handpiece 81 to the tip 82 and fit the rim 98 of the shield 95 through the aperture 73 in its enlarged state so that the elastic member 73b preferably rests around the collar 97. The elastic member 73b preferably generates a gripping force on the collar to substantially prevent the elastic member 73b from sliding along the collar 97. Personnel optionally shorten the length 76 of the sheet 71 as desired. For example, personnel can cut the sheet 71 a desired distance circumferentially around the axis 72. Medical personnel preferably cut the sheet 71 with scissors, but may optionally use any sharp object.

Medical personnel then place the open end 74 of the sheet 71 so that it is disposed over the wound region of the patient. For example, if the wound is on the knee-area, as discussed above, personnel can place the sheet 71 over the injured leg of the patient so that it covers the wound area and the basin 10. Personnel then actuate the irrigation device by pressing the trigger 93 to emit irrigation fluid from the tip 82. Irrigation fluid is then directed to the wound area of the patient, which is then collected in the basin.

It is to be noted that the illustrated irrigation device 80 is merely an example of irrigation devices used in the surgical arts. The aperture 73 can be sized to fit over and engage any type of irrigation device, including those without a suction or aspiration feature, and those with different sizes and types of splash shields, or with or without a splash shield.

With reference to FIGS. 14-20, a prior art suction system is described below with reference to FIGS. 14-19. An improved suction hose is illustrated in FIG. 20, in section view and identified generally by the reference numeral 5'.

With reference to FIG. 14, a typical suction system used in an operating room includes a suction source 110, a suction hose 112 having a first end connected to the suction source and a second end 114 which includes a female adapter configured to releasably engage a fluid and debris collection device 116.

The fluid and debris collection device 116 is typically in the form of a glass jar 118 having a lid 120. The lid 120 includes a connector 122 configured to create a seal with the adapter 114. The lid 120 typically includes at least one other adapter 124 that is configured to connect with a female connector typically included with suction hose typically used in an operating room.

FIG. 15 shows an enlarged side elevational view of a female connector 126 connected to an end of suction hose 128. The suction hose 128 has an inner diameter 130 of about 6 millimeters. The outer diameter 132 of the hose 128 is about 9 millimeters.

The female adapter 126 includes a first annular recess 134 that is configured to mate with the outer surface of the tubing 128. The female adapter 126 also includes a stop member 136 that is configured to abut the inner end of the hose 128. The inner surface 138 of the stop 136 is sized so as to define an inner diameter that is approximately equal to the inner diameter 130. The female adapter 126 also includes an inner recess 140 that is configured to receive the adapter 124 (FIG. 14). The opposite end of the hose 128 can include another female adapter similar or identical to the female adapter 126.

As shown in FIG. 16, a suction device 142 which is commonly used in medical procedures, includes an inlet end 144 and a discharge end 146. The inlet end 144 includes a plurality of openings 148, opening into an inner lumen 150. The openings 148 are sized to prevent large clumps of tissue and bone chips from entering the lumen 150. For example, one known suction device includes openings that are about 4 m long and 1-2 mm wide.

The lumen 150 extends along the length of the suction device 142 and terminates at a discharge 146. The discharge 146 is configured to fit into a recess of a female adapter such as the recess 140 in the female adapter 126 (FIG. 15).

In an operation, the vacuum hose 128 connects the suction device 142 with the adapter 124 of the debris collector 116. With the suction source 110 activated, a vacuum is created in the interior of the collection device 116, thereby drawing a vacuum through the adapter 124, through the vacuum hose 128 and through the suction device 142. As such, fluid and debris is drawn through the apertures 148, through the lumen 150, through the hose 128 and into the interior of the collection device 116. Because the adapter 122 is mounted to the lid 120, the fluid and debris collected within the jar 118 does not enter the hose 112 or the suction source 110.

However, it has been found that the suction hose 128 that is typically used in operating rooms can become clogged more easily than the suction device 142. Further, it is also been found that clogs within the suction hose 128 can be initiated at deformed portions of the house 128.

For example, with reference to FIG. 17, a suction hose kit 152 is illustrated therein and includes a sterilized package 154 and the suction tubing 128. It has been found that such conventional suction tubing 128 can become deformed. For example, some portions of such suction tubing 128 remains round in sections.

As shown in FIG. 18, the cross-sectional shape of the tubing 128 in certain areas remains round. However, as shown in FIG. 19, certain portions of the tubing 128 can become constricted. This deformation can sometimes be found in the curve of the tubing 128 that has been folded for packaging purposes so that the tubing 128 fits within the package 154. Additionally, various portions of the tubing 128 can include indentations that may have been formed by machines used to manufacture the tubing 128 or from the weight of other articles stacked on top of the package 154 during stocking. Regardless of the mechanism causing such deformation, an inner dimension 156 of the deformed portion of the tube 128 can become sufficiently restricted that the likelihood of clogging at the deformed portion is increased.

Thus, in accordance with an aspect of at least one of the inventions disclosed herein, a suction tubing 5' illustrated in FIG. 20 includes an inner diameter of at least about 8 millimeters. More preferably, the inner diameter of the tubing 5' is from about 8 millimeters to about 15 millimeters.

As such, the tubing 5' can include the same type of deformations occurring in the known suction tubing 128, yet retain a sufficient clearance within its inner dimension that the likelihood of clogging is not increased as greatly as that resulting from the deformed portions of the tubing 128 illustrated in FIG. 19. For example, were the suction tubing 5' is formed with an inner diameter of about 8 millimeters in a relaxed state, the suction tubing 5' can be deformed to some extent resulting in a minimum inner dimension identified by the reference numeral 158. Because the diameter of the suction tubing 5' in a relaxed state is at least 8 millimeters, the reduced inner dimension 158 caused by a deformation can still be as large as 6 millimeters. Thus, where the tubing 5' has been damaged or deformed in the same manner as the known tubing 128, the tubing 5' is less likely to cause clogging in the same manner as the known tubing 128.

Optionally, the tubing 5' can include the same female connectors 126 described above with reference to FIG. 15. However, such female adapters can also include slight modifications to the inner recess 134 so as to more readily accept the outer diameter of the tubing 5'.

In another modification, a female adapter included with the tubing 5' can define a larger inner diameter than the inner surface 138 of the adapter 126. In use, it may be preferable to cut the adapter 124 so as to avoid the formation of a bottle neck in the vacuum circuit leading to the container 116.

Although the inventions disclosed herein have been disclosed in the context of certain preferred embodiments and examples, it will be understood by those skilled in the art that the inventions disclosed herein extend beyond the specifically disclosed embodiments to other alternative embodiments and/or uses of the inventions and obvious modifications and equivalents thereof. Thus, it is intended that the scope of the inventions disclosed herein should not be limited by the particular disclosed embodiments described above, but should be determined only by a fair reading of the embodiments that follow.

What is claimed is:

1. A medical basin for collecting fluid during an irrigation procedure of a wound on a human extremity, the basin being sterilized and comprising:
    a base;
    a peripheral wall comprising:
        an inner surface defining a cavity configured to receive the irrigation fluid during the irrigation procedure;
        an upper edge defining an upper periphery;
        a lower edge;
        a first side; and
        a second side;
        wherein a portion of the peripheral wall defines a contact region, the contact region being thinner at an upper edge thereof than at a lower portion thereof;
    a first contoured recess formed on the first side of the peripheral wall, the first contoured recess configured to receive a first portion of the human extremity on a first side of a joint in the extremity;
    a connection element configured to connect with a suction hose to facilitate removal of irrigation fluid from the basin during the irrigation procedure of the wound on the human extremity received the basin; and
    wherein the basin is generally rectangular in shape and has a length and a height, the ratio of the length to the height being at least 3.

2. The medical basin of claim 1, wherein the basin further has a width, the ratio of the width to the height being at least 2.5.

3. The medical basin of claim 1, wherein the recess has a minimum height, the ratio of the length of the basin to the minimum height of the recess of the basin being at least 5.

4. The medical basin of claim 1, further comprising a second contoured recess formed opposite the first contoured recess on a second side of the peripheral wall of the basin, the second contoured recess configured to receive a second portion of the human extremity on a second side of the joint.

5. The medical basin of claim 1, wherein:
    the base comprises a generally flat bottom surface configured to rest on a resting surface at substantially at zero degrees relative to the resting surface; and
    the base comprises a generally flat top surface that is substantially parallel with the bottom surface.

* * * * *